United States Patent
Giftakis et al.

(10) Patent No.: US 12,036,401 B2
(45) Date of Patent: Jul. 16, 2024

(54) SEIZURE DETECTION ALGORITHM ADJUSTMENT

(71) Applicant: Medtronic, Inc., Minneapolis, MN (US)

(72) Inventors: Jonathon E. Giftakis, Maple Grove, MN (US); Nathan A. Torgerson, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 1208 days.

(21) Appl. No.: 16/773,719

(22) Filed: Jan. 27, 2020

(65) Prior Publication Data
US 2020/0155829 A1    May 21, 2020

Related U.S. Application Data

(63) Continuation of application No. 12/432,268, filed on Apr. 29, 2009, now Pat. No. 10,543,359.
(Continued)

(51) Int. Cl.
*A61N 1/05*      (2006.01)
*A61B 5/00*      (2006.01)
(Continued)

(52) U.S. Cl.
CPC ............ *A61N 1/0534* (2013.01); *A61B 5/031* (2013.01); *A61B 5/4094* (2013.01); *A61N 1/36082* (2013.01)

(58) Field of Classification Search
CPC ....... A61B 5/4094; A61B 5/369; A61B 5/374; A61B 5/291; A61N 1/36064; A61N 1/36025
See application file for complete search history.

(56) References Cited

U.S. PATENT DOCUMENTS 4,080,653 A    3/1978   Barnes, Jr. et al.
4,320,766 A    3/1982   Alihanka et al.
(Continued)

FOREIGN PATENT DOCUMENTS

WO      9742990      11/1997
WO      2006119103 A2   11/2006
(Continued)

OTHER PUBLICATIONS

"Intracranial pressure," Wikipedia, the free encyclopedia, accessed from web.archive.org/web/20071016060909/http://en.wikipedia.org/wiki/Intracranial_pressure, dated Sep. 28, 2007, retrieved on Oct. 16, 2007, 6 pp.
(Continued)

*Primary Examiner* — Tse W Chen
*Assistant Examiner* — Michael A Catina
(74) *Attorney, Agent, or Firm* — Shumaker & Sieffert, P.A.

(57) ABSTRACT

A medical system implements a seizure detection algorithm to detect a seizure based on a first patient parameter. The medical system monitors a second patient parameter to adjust the seizure detection algorithm. In some examples, the medical system determines whether a seizure for which therapy delivery is desirable occurred based on a second patient parameter. If a target seizure occurred, and the seizure detection algorithm did not detect the target seizure, the medical system adjusts the seizure detection algorithm to detect the target seizure. For example, the medical system may determine a first patient parameter characteristic indicative of the target seizure detected based on the second patient parameter and store the first patient parameter characteristic as part of the seizure detection algorithm. In some examples, the first patient parameter is an electrical brain signal and the
(Continued)

second patient parameter is patient activity (e.g., patient motion or posture).

23 Claims, 9 Drawing Sheets

Related U.S. Application Data

(60) Provisional application No. 61/113,441, filed on Nov. 11, 2008.

(51) Int. Cl.
*A61B 5/03* (2006.01)
*A61N 1/36* (2006.01)

(56) References Cited

U.S. PATENT DOCUMENTS

| | | | |
|---|---|---|---|
| 4,971,061 A | 11/1990 | Kageyama et al. | |
| 5,304,206 A | 4/1994 | Baker, Jr. et al. | |
| 5,349,962 A | 9/1994 | Lockard et al. | |
| 5,978,702 A | 11/1999 | Ward et al. | |
| 5,995,868 A | 11/1999 | Dorfmeister et al. | |
| 6,248,080 B1 | 6/2001 | Miesel et al. | |
| 6,360,122 B1 | 3/2002 | Fischell et al. | |
| 6,361,508 B1 | 3/2002 | Johnson et al. | |
| 6,560,486 B1 | 5/2003 | Osorio et al. | |
| 6,788,975 B1 | 9/2004 | Whitehurst et al. | |
| 7,006,872 B2 | 2/2006 | Gielen et al. | |
| 7,167,751 B1 | 1/2007 | Whitehurst et al. | |
| 7,519,431 B2 | 4/2009 | Goetz et al. | |
| 8,376,943 B2 | 2/2013 | Kovach et al. | |
| 9,788,750 B2 | 10/2017 | Denison et al. | |
| 10,369,353 B2 | 8/2019 | Giftakis et al. | |
| 10,543,359 B2 | 1/2020 | Giftakis et al. | |
| 2002/0052563 A1 | 5/2002 | Penn et al. | |
| 2002/0169485 A1 | 11/2002 | Pless et al. | |
| 2003/0236474 A1 | 12/2003 | Singh | |
| 2004/0172089 A1 | 9/2004 | Whitehurst et al. | |
| 2005/0015009 A1 | 1/2005 | Mourad et al. | |
| 2005/0197590 A1* | 9/2005 | Osorio | A61B 5/4094 600/544 |
| 2005/0203366 A1* | 9/2005 | Donoghue | A61B 5/6814 607/46 |
| 2006/0135877 A1* | 6/2006 | Giftakis | A61N 1/36521 600/513 |
| 2006/0212093 A1 | 9/2006 | Pless et al. | |
| 2006/0264777 A1 | 11/2006 | Drew | |
| 2007/0238939 A1* | 10/2007 | Giftakis | A61N 1/39622 600/301 |
| 2007/0239230 A1* | 10/2007 | Giftakis | A61B 5/369 607/62 |
| 2007/0249954 A1 | 10/2007 | Virag et al. | |
| 2007/0255118 A1 | 11/2007 | Miesel et al. | |
| 2007/0276439 A1 | 11/2007 | Miesel et al. | |
| 2008/0061961 A1 | 3/2008 | John | |
| 2008/0071324 A1 | 3/2008 | Miesel et al. | |
| 2008/0319281 A1 | 12/2008 | Aarts | |
| 2008/0319335 A1 | 12/2008 | Greene | |
| 2009/0062696 A1* | 3/2009 | Nathan | A61B 5/7282 600/595 |
| 2009/0082640 A1 | 3/2009 | Kovach et al. | |
| 2009/0099624 A1 | 4/2009 | Kokones et al. | |
| 2009/0171168 A1* | 7/2009 | Leyde | A61B 5/291 600/301 |
| 2010/0121214 A1 | 5/2010 | Giftakis et al. | |
| 2012/0053491 A1 | 3/2012 | Nathan et al. | |

FOREIGN PATENT DOCUMENTS

| | | |
|---|---|---|
| WO | 2007034476 A3 | 3/2007 |
| WO | 2008085008 A1 | 7/2008 |
| WO | 2008133626 A1 | 11/2008 |

OTHER PUBLICATIONS

Azar et al., "Postictal breathing pattern distinguishes epileptic from nonepileptic convulsive seizures," Epilepsia, 49(1):132-137, Jan. 2008, online early publication Jul. 25, 2007, 6 pp.

Berg et al., "Newly Diagnosed Epilepsy in Children: Presentation at Diagnosis," Epilepsia, 40(4):445-452, Apr. 1999, 8 pp.

Cuppens et al., "Detection of Nocturnal Epileptic Seizures of Pediatric Patients Using Accelerometers: Preliminary Results," IEEE Benelux EMBS Symposium, 4 pgs., Dec. 6-7, 2007.

Gabor et al., "Intracranial Pressure During Epileptic Seizures," Electroencephalography and clinical Neurophysiology, 57, pp. 497-506 (Jan. 1984).

Prosecution History from U.S. Appl. No. 12/432,268, dated Nov. 16, 2011 through Jan. 9, 2020, 328 pp.

Sen et al., "Stertorous breathing is a reliably identified sign that helps in the differentiation of epileptic from psychogenic non-epileptic convulsions: An audit," Epilepsy Research, Sep. 2007, 62-64 pp.

Tormans et al., "Nocturnal Monitoring of Pediatric Patients with Epilepsy based on Accelerometers," accessed from http://www.mobilab-khk.be/mobilab/Research/BioMed/Projects/epileptic, accessed on Mar. 31, 2009, 2 pp.

Tormans et al., "Nocturnal Monitoring of Pediatric Patients with Epilepsy Based on Accelerometers," Nov. 2007, 3 pp.

* cited by examiner

SEIZURE DETECTION ALGORITHM ADJUSTMENT

This application is a continuation of U.S. patent application Ser. No. 12/432,268 by Giftakis et al., entitled "SEIZURE DETECTION ALGORITHM ADJUSTMENT" and filed on Apr. 29, 2009, which claims the benefit of U.S. Provisional Application No. 61/113,441 by Giftakis et al., entitled "SEIZURE DISORDER EVALUATION BASED ON INTRACRANIAL PRESSURE AND PATIENT MOTION" and filed on Nov. 11, 2008. The entire contents of application Ser. No. 12/432,268 and 61/113,441 are incorporated herein by reference.

TECHNICAL FIELD

The disclosure relates to therapy delivery, and, more particularly, to configuration of therapy parameters.

BACKGROUND

Some neurological disorders, such as epilepsy, are characterized by the occurrence of seizures. Seizures may be attributable to abnormal electrical activity of a group of brain cells. A seizure may occur when the electrical activity of certain regions of the brain, or even the entire brain, becomes abnormally synchronized. The onset of a seizure may be debilitating. For example, the onset of a seizure may result in involuntary changes in body movement, body function, sensation, awareness or behavior (e.g., an altered mental state). In some cases, each seizure may cause some damage to the brain, which may result in progressive loss of brain function over time.

Attempts to manage seizures have included the delivery of electrical stimulation to regions of the brain and/or the delivery of drugs either orally or infused directly into regions of the brain. In electrical stimulation systems, a medical lead is implanted within a patient and coupled to an external or implanted electrical stimulator. The target stimulation site within the brain or elsewhere may differ between patients, and may depend upon the type of seizures being treated by the electrical stimulation system. In some therapy systems, electrical stimulation is continuously delivered to the brain. In other systems, the delivery of electrical stimulation is triggered by the detection or prediction of some event, such as the detection of a seizure based on bioelectrical brain signals sensed within the brain.

In automatic drug delivery systems, a catheter is implanted within a patient and coupled to an external or implanted fluid delivery device. The fluid delivery device may deliver a dose of an anti-seizure drug into the blood stream or into a region of the brain of the patient at regular intervals, upon the detection or prediction of some event, such as the detection of a seizure by electroencephalogram (EEG) or electrocorticogram (ECG) sensors implanted within the brain, or at the direction of the patient or clinician.

SUMMARY

In general, the disclosure is directed toward therapy delivery to manage a seizure disorder of a patient and monitoring of a seizure disorder of the patient. A medical system implements a seizure detection algorithm to detect a seizure (e.g., the onset of a seizure or the possibility of a seizure onset) based on a first patient parameter, which may be a physiological parameter. The medical system controls therapy delivery to the patient upon detecting the seizure based on the first patient parameter. The medical system also monitors a second patient parameter to adjust the seizure detection algorithm. In some examples, the medical system determines whether a seizure for which therapy delivery is desirable, referred to herein as a target seizure, occurred based on a second patient parameter, which may or may not be a physiological parameter. In some examples, the first patient parameter is an electrical brain signal and the second patient parameter is patient activity (e.g., patient motion or posture).

If the second patient parameter indicates a target seizure occurred and the medical system, while implementing the seizure detection algorithm, did not detect the target seizure based on the first patient parameter, the medical system adjusts the seizure detection algorithm to detect the target seizure. In some examples, identification of target seizures based on the second patient parameter may indicate whether a seizure detection algorithm for detecting a seizure is too sensitive (e.g., resulting in the mischaracterization of certain patient activity as target seizures) or not sufficiently sensitive (e.g., resulting in the failure to detect one or more target seizures).

In one aspect, the disclosure is directed to a method comprising receiving a bioelectrical brain signal of a patient sensed by a medical device, receiving a patient activity signal indicative of motor (e.g., physical) activity of the patient, identifying a target seizure based on the patient activity signal, and determining a characteristic of the bioelectrical brain signal that is indicative of the target seizure.

In another aspect, the disclosure is directed to a method comprising receiving a first signal indicative of a physiological parameter of a patient, receiving a second signal indicative of a patient parameter of the patient, and adjusting a seizure detection algorithm of a medical device based on the first and second signals. The medical device implements the seizure detection algorithm to detect the target seizure based on the first signal.

In another aspect, the disclosure is directed to a system comprising a first sensor that senses a bioelectrical brain signal of a patient, a second sensor that generates a patient activity signal, and a processor that receives the bioelectrical brain signal and the patient activity signal, identifies a target seizure based on the patient activity signal, and determines a characteristic of the bioelectrical brain signal that is indicative of the target seizure.

In another aspect, the disclosure is directed to a system comprising a first sensor that generates a first signal indicative of a physiological parameter of a patient, a second sensor that generates a second signal indicative of a patient parameter of the patient, and a processor that receives the first and second signals and adjusts a seizure detection algorithm of a medical device based on the first and second signals.

In another aspect, the disclosure is directed to a system comprising means for receiving a bioelectrical brain signal of a patient sensed by a medical device, means for receiving a patient activity signal indicative of movement of the patient, means for identifying a target seizure based on the patient activity signal, and means for determining a characteristic of the bioelectrical brain signal that is indicative of the target seizure.

In another aspect, the disclosure is directed to a system comprising means for generating a first signal indicative of a physiological parameter of a patient, means for generating a second signal indicative of a patient parameter of the patient, and means for adjusting a seizure detection algorithm based on the first and second signals.

In another aspect, the disclosure is directed to a computer-readable storage medium comprising instructions. The instructions cause a programmable processor to receive a bioelectrical brain signal of a patient sensed by a medical device, receive a patient activity signal indicative of motor activity of the patient, identify a target seizure based on the patient activity signal, and determine a characteristic of the bioelectrical brain signal that is indicative of the target seizure.

In another aspect, the disclosure is directed to a computer-readable storage medium comprising instructions. The instructions cause a programmable processor to receive a first signal indicative of a physiological parameter of a patient, receive a second signal indicative of a patient parameter of the patient, and adjust a seizure detection algorithm based on the first and second signals.

In another aspect, the disclosure is directed to a computer-readable storage medium comprising instructions. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, random access memory or RAM) or any other type of volatile or non-volatile memory that stores instructions (e.g., in the form of a computer program or other executable) to cause a programmable processor to perform the techniques described herein.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
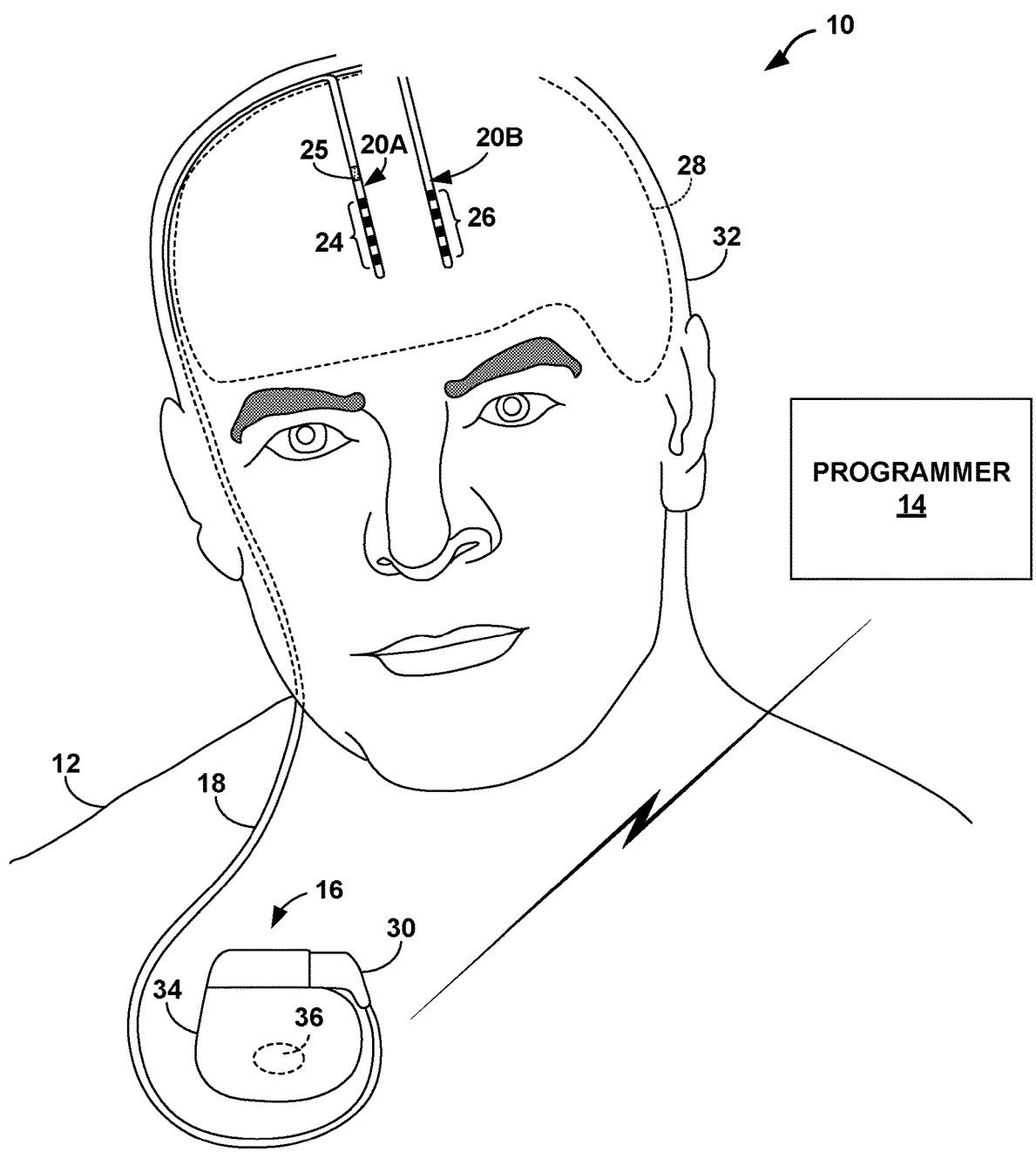
FIG. 1 is a conceptual diagram illustrating an example deep brain stimulation (DBS) system that includes one or more activity sensors that generate a signal indicative of patient activity.

A therapy system may be used to manage a seizure disorder of a patient, e.g., to mitigate the effects of the seizure disorder, shorten the duration of seizures, prevent the onset of seizures or notify a patient about an onset or potential onset of a seizure. In some therapy systems described herein, a medical device implements a seizure detection algorithm to detect a seizure based on a first patient parameter, which may be a physiological parameter (e.g., a bioelectrical brain signal). The medical device may deliver therapy to a patient or generate an alert upon detecting the onset of a seizure or the potential onset of a seizure based on the first patient parameter. Examples of bioelectrical brain signals that may be used to detect an onset of a seizure or a potential seizure onset include tissue impedance, an electrical encephalogram (EEG), an electrocorticogram (ECoG), a local field potential (LFP) sensed from within one or more regions of a patient's brain and/or action potentials from single cells within the patient's brain. In other examples, a medical system may implement a seizure detection algorithm based on other physiological parameters, such as heart rate or other suitable physiological parameters that change prior to or upon the onset of a seizure or prior to the onset of a seizure. A medical device, medical device programmer, another computing device or any combination thereof may implement the seizure detection algorithms described herein.

In general, it is desirable to limit the number of false positive seizure detections (i.e., the incorrect detection of a seizure) and false negative seizure detections (i.e., the failure to detect a seizure) by the medical device. Techniques described herein may be used to adjust the seizure detection algorithm implemented by the medical device in order to minimize the number of false positive seizure detections and false negative seizure detections. As described in further detail below, some techniques described herein include monitoring a second patient parameter in order to determine whether the medical device is failing to detect seizures for which therapy delivery is desirable, referred to herein as target seizures, or is delivering therapy to the patient when a target seizure is not occurring. While actual therapy delivery is controlled based on whether the first patient parameter is indicative of a seizure, the seizure detection algorithm may be adjusted (e.g., refined or updated) based on the second patient parameter to better detect seizures and minimize false negative and false positive seizure detections.

The second patient parameter that is an indicator of a seizure occurrence is used to adjust the seizure detection algorithm that relies on the first patient parameter, but not the second patient parameter, to detect seizures. The second patient parameter is considered to be a relatively reliable indicator of a seizure because it is detects the results of a seizure while the seizure is actually occurring. These results may include, for example, physical patient activity (motor activity). In contrast to the second patient parameter, the first patient parameter monitors a patient parameter that indicates the seizure that occurs before the physical manifestations of the seizure. Thus, the first patient parameter is suitable for driving a course of action (e.g., therapy delivery or a warning) in order to either prevent the seizure or mitigate the severity of the seizure (e.g., by providing stimulation therapy) or to provide a warning to the patient that a seizure is about to occur so that the patient can get to a safe position prior to the onset of any debilitating effects of the seizure.

In some examples, a medical device automatically adjusts a seizure detection algorithm in accordance with the techniques described herein. In other examples, the medical device adjusts the seizure detection algorithm upon receive instructions from a user (e.g., a clinician or patient). A programmer or another computing device may also adjust a seizure detection algorithm in accordance with the techniques described herein. In addition, in some examples, therapeutic efficacy can be evaluated based on a number of target seizures detected based on the first and second patient parameters.

In the examples described herein, the first patient parameter includes a bioelectrical brain signal. Thus, the examples described here describe seizure detection algorithms that detect a seizure based on bioelectrical brain signals. However, in other examples, the first patient parameter may include one or more other physiological parameters instead of or in addition to bioelectrical brain signals.

In addition, in the examples described herein, the second patient parameter that is monitored in order to adjust a seizure detection algorithm includes a patient parameter that indicates the occurrence of a target seizure by, for example, indicating the occurrence of physical manifestations of the seizure. Thus, in some examples, the second patient parameter includes motor activity (e.g., patient motion or posture). In other examples, the second patient parameter may include one or more other physiological parameters instead of or in addition to patient activity. For example, in other examples, a seizure detection algorithm may be updated based on target seizures detected based on respiration rate, heart rate, muscle activity (e.g., determined based on an electromyogram (EMG)), intracranial pressure, and other physiological parameters that may change upon the onset of a seizure.

Respiration rate and heart may increase upon the occurrence of a target seizure, such as a seizure associated with a motor component (e.g., a tonic-clonic seizure). In addition, muscle activity of the patient may exhibit a certain pattern (e.g., a repetitive pattern) or a sudden increase in activity level upon the occurrence of a target seizure. A sudden change in intracranial pressure may also indicate the occurrence of a target seizure, e.g., by indicating a sudden change in patient posture that resulted from the seizure (e.g., from a fall associated with the seizure). In some cases, a sudden increase in intracranial pressure may indicate the occurrence of a target seizure, e.g., because of an increased volume of cerebral spinal fluid or blood in the brain of the patient. An elevated or high respiration rate, heart rate, muscle activity or intracranial pressure may be determined based on comparison of respective values to a threshold value.

Example devices, systems, and techniques for monitoring intracranial pressure of a patient and monitoring a seizure disorder of a patient are described in U.S. patent application Ser. Nos. 12/359,037 and 12/359,055 to Giftakis et al., which are both entitled, "SEIZURE DISORDER EVALUATION BASED ON INTRACRANIAL PRESSURE AND PATIENT MOTION" and were both filed on Jan. 23, 2009. U.S. patent application Ser. Nos. 12/359,037 and 12/359,055 to Giftakis et al. are incorporated herein by reference in their entireties.

FIG. 1 is a conceptual diagram illustrating an example therapy system 10 that delivers therapy to manage a seizure disorder (e.g., epilepsy) of patient 12. Patient 12 ordinarily will be a human patient. In some cases, however, therapy system 10 may be applied to other mammalian or non-mammalian non-human patients. While seizure disorders are primarily referred to herein, in other examples, therapy system 10 may also provide therapy to manage symptoms of other patient conditions in addition to a seizure disorder, such as, but not limited to, psychological disorders, movement disorders or other neurogenerative impairment.

Therapy system 10 may be used to manage the seizure disorder of patient 12 by, for example, minimizing the severity of seizures, shortening the duration of seizures, minimizing the frequency of seizures, preventing the onset of seizures, and the like. Therapy system 10 includes medical device programmer 14, implantable medical device (IMD) 16, lead extension 18, and one or more leads 20A and 20B with respective sets of electrodes 24, 26. In addition to delivering therapy to manage a seizure, therapy system 10 monitors patient posture and activity, such as with the aid of one or more two-axis or three-axis accelerometers, piezoelectric crystals or pressure transducers. In some examples, a therapy delivery element, such as lead 20A, includes an activity sensor 25 to monitor patient activity (e.g., motion or posture).

IMD 16 includes a therapy module that comprises a stimulation generator that generates and delivers electrical stimulation therapy to patient 12 via a subset of electrodes 24, 26 of leads 20A and 20B, respectively. In the example shown in FIG. 1, electrodes 24, 26 of leads 20A, 20B are positioned to deliver electrical stimulation to a tissue site within brain 28, such as a deep brain site under the dura mater of brain 28 of patient 12. In some examples, delivery of stimulation to one or more regions of brain 28, such as an anterior nucleus, thalamus or cortex of brain 28, may provide an effective treatment to manage a seizure disorder.

IMD 16 may include a sensing module that senses bioelectrical signals within brain 28. The bioelectrical brain signals may reflect changes in electrical current produced by the sum of electrical potential differences across brain tissue. Examples of bioelectrical brain signals include, but are not limited to, an EEG signal, ECoG signal, a LFP sensed from within one or more regions of a patient's brain and/or action potentials from single cells within the patient's brain. In addition, in some cases, a bioelectrical brains signal includes a measured impedance of tissue of brain 28.

In the example shown in FIG. 1, IMD 16 implements a seizure detection algorithm to detect an onset of a seizure or a possibility of a seizure onset based on the bioelectrical brain signal. In general, the detection of an onset of a seizure or a potential seizure onset may be referred to as a detection of a seizure. In some examples, IMD 16 may detect the seizure based on the bioelectrical brain signal prior to the actual physical manifestations of the seizure being perceived by patient 12 or being indicated by the second patient parameter. Upon detecting the seizure, IMD 16 delivers therapy to brain 28 of patient 12 to help mitigate the effects of the seizure or, in some cases, prevent the onset of the seizure or manifestations of the seizure that are perceived by patient 12. In this way, the bioelectrical brain signals may be used to control therapy delivery to patient 12. Seizure detection by IMD 16 using the seizure detection algorithm may include receiving bioelectrical electrical signals monitored within brain 28 of patient 12, analyzing the input signals, and producing an output that triggers the delivery of therapy or generation of a patient alert.

One type of seizure detection algorithm indicates a seizure upon sensing of a bioelectrical brain signal that exhibits a certain characteristic, which may be a time domain characteristic (e.g., an amplitude) or a frequency domain characteristic (e.g., an energy level in one or more frequency bands). For example, the seizure detection algorithm may indicate that a seizure is detected when the amplitude of the bioelectrical brain signal meets a certain condition relative to a threshold (e.g., is greater than, equal to or less than the threshold). Another example seizure detection algorithm detects a seizure onset if a sensed bioelectrical brain signal substantially correlates to a signal template (e.g., in terms of frequency, amplitude and/or spectral energy characteristics).

IMD 16 may use known techniques to correlate a sensed bioelectrical signal with a template in order to detect a seizure or detect a seizure based on the frequency domain characteristics of a sensed bioelectrical brain signal. Other seizure detection techniques may be used.

An example disclosure that describes detecting a brain signal characteristic indicative of a seizure and are described in commonly-assigned U.S. Pat. No. 7,006,872 to Gielen et al., entitled, "CLOSED LOOP NEUROMODULATION FOR SUPPRESSION OF EPILEPTIC ACTIVITY," which issued on Feb. 28, 2006. U.S. Pat. No. 7,006,872 to Gielen et al. is incorporated herein by reference in its entirety. In some examples described in U.S. Pat. No. 7,006,872 to Gielen et al., a seizure is predicted based on whether a sensed EEG starts to show synchrony as opposed to the normal stochastic features. As described in U.S. Pat. No. 7,006,872 to Gielen et al., therapy may be delivered when the EEG data exhibits a certain characteristic indicative of a likelihood of an onset of a seizure.

Another example of a seizure detection algorithm that IMD 16 may implement to detect a seizure is described in commonly-assigned U.S. patent application Ser. No. 11/799,051 to Denison et al., which is entitled, "SEIZURE PREDICTION" and was filed on Apr. 30, 2007. U.S. patent application Ser. No. 11/799,051 to Denison et al. is incorporated herein by reference in its entirety. In an example technique described in U.S. patent application Ser. No. 11/799,051 to Denison et al., a likelihood of an onset of a seizure is determined based on an impedance of one or more regions of brain 28 of patient 12. In some examples described in U.S. patent application Ser. No. 11/799,051 to Denison et al., a relationship between the measured impedance of the brain and an absolute threshold impedance value is used to predict a seizure. In other examples described in U.S. patent application Ser. No. 11/799,051 to Denison et al., a measured impedance signal over time is analyzed for slope, amplitude, temporal correlation or frequency correlation with a template signal, or combinations thereof in order to determine whether a seizure is likely to occur. In some examples, IMD 16 may include an impedance sensing module to sense impedance of brain tissue.

IMD 16 may determine impedance of tissue within brain 28 based on signals sensed via any suitable combination of electrodes 24, 26. For example, as described in U.S. patent application Ser. No. 11/799,051 to Denison et al., an impedance of brain 28 of patient 12 is measured by delivering a stimulation current to brain 28 via implanted electrodes. The stimulation current may be relatively low to prevent inadvertent stimulation of tissue and to prevent patient 12 from feeling the stimulation current. For example, the stimulation current may be in a range of about 500 nanoamps (nA) to about 10 microamps (μA), although other stimulation currents may be used. The stimulation current that is delivered to measure impedance may differ from that used to deliver stimulation therapy to the patient to prevent a seizure from occurring or to mitigate the effects of a seizure. As described in U.S. patent application Ser. No. 11/799,051 to Denison et al., examples of frequencies that may be used for the input stimulation current to measure impedance of the brain include, but are not limited to range of about 1 kilohertz (kHz) to about 100 kHz, such as a range of about 4 kHz to about 16 kHz.

IMD 16 may be implanted within a subcutaneous pocket above the clavicle, or, alternatively, the abdomen, back or buttocks of patient 12, on or within cranium 32 or at any other suitable site within patient 12. Generally, IMD 16 is constructed of a biocompatible material that resists corrosion and degradation from bodily fluids. IMD 16 may comprise a hermetic outer housing 34 to substantially enclose components, such as a processor, therapy module, and memory.

Implanted lead extension 18 is coupled to IMD 16 via connector 30. In the example of FIG. 1, lead extension 18 traverses from the implant site of IMD 16 and along the neck of patient 12 to cranium 32 of patient 12 to access brain 28. Lead extension 18 is electrically and mechanically connected to leads 20A, 20B (collectively "leads 20"). In the example shown in FIG. 1, leads 20 are implanted within the right and left hemispheres, respectively, of patient 12 in order to deliver electrical stimulation to one or more regions of brain 28, which may be selected based on the patient condition or disorder controlled by therapy system 10. Other implant sites for leads 20 and IMD 16 are contemplated. For example, IMD 16 may be implanted on or within cranium 32 or leads 20 may be implanted within the same hemisphere or IMD 16 may be coupled to a single lead. Although leads 20 are shown in FIG. 1 as being coupled to a common lead extension 18, in other examples, leads 20 may be coupled to IMD 16 via separate lead extensions or directly connected to connector 30 of IMD 16. In addition, in some examples, therapy system 10 may include more than two leads or one lead.

Leads 20 may be positioned to deliver electrical stimulation to one or more target tissue sites within brain 28 to manage patient symptoms associated with a seizure disorder of patient 12. Leads 20 may be implanted to position electrodes 24, 26 at desired locations of brain 28 through respective holes in cranium 32. Leads 20 may be placed at any location within brain 28 such that electrodes 24, 26 are capable of providing electrical stimulation to target tissue sites within brain 28 during treatment. For example, electrodes 24, 26 may be surgically implanted under the dura mater of brain 28 via a burr hole in cranium 32 of patient 12, and electrically coupled to IMD 16 via one or more leads 20.

In the example shown in FIG. 1, electrodes 24, 26 of leads 20 are shown as ring electrodes. Ring electrodes may be useful in deep brain stimulation applications because they are relatively simple to program and are capable of delivering an electrical field to any tissue adjacent to electrodes 24, 26. In other examples, electrodes 24, 26 may have different configurations. For examples, in some examples, at least some of the electrodes 24, 26 of leads 20 have a complex electrode array geometry that is capable of producing shaped electrical fields. The complex electrode array geometry may include multiple electrodes (e.g., partial ring or segmented electrodes) around the outer perimeter of each lead 20, rather than one ring electrode. In this manner, electrical stimulation may be directed to a specific direction from leads 20 to enhance therapy efficacy and reduce possible adverse side effects from stimulating a large volume of tissue. In some examples, housing 34 of IMD 16 includes one or more stimulation and/or sensing electrodes. In alternative examples, leads 20 may have shapes other than elongated cylinders as shown in FIG. 1. For example, leads 20 may be paddle leads, spherical leads, bendable leads, or any other type of shape effective in treating patient 12.

Activity sensor 25, which is coupled to lead 20A, generates a signal indicative of patient activity (e.g., patient movement or patient posture transitions). For example, activity sensor 25 may include one or more accelerometers, such as one or more single-axis, two-axis or three-axis accelerometers, capable of detecting static orientation or vectors in three-dimensions. An example accelerometer is a micro-electromechanical accelerometer. In other examples, activity sensor 25 may alternatively or additionally include one or more gyroscopes, pressure transducers, piezoelectric crystals, or other sensors that generate a signal that changes as a function of patient activity.

When activity sensor 25 is positioned within cranium 32, activity sensor 25 may generate an electrical signal indicative of movement of the head of patient 12. For some patients, certain types of seizures may result in a pulling action of the head. Thus, activity sensor 25 may be used to detect seizures that include such pulling action. Activity sensor 25 may also generate an electrical signal indicative of convulsive motion of patient 12. For some patients, certain types of seizures (e.g., a tonic-clonic seizure) may result in the patient undergoing involuntary, convulsive movement. The convulsive movement may include, for example, twitching or violent shaking of the arms, legs, and/or head.

Although FIG. 1 illustrates activity sensor 25 located proximal to electrodes 24, 26 on leads 20, in other examples, electrodes 24, 26 and activity sensor 25 may have any suitable arrangement. For example, one or more activity sensors may be located between one or more electrodes 24, 26, respectively. As another example, one or more activity sensors may be located distal to one or more electrodes 24, 26. A therapy system may include an activity sensor that is physically separate from leads 20 that deliver therapy to patient 12, and communicates with IMD 16 via wireless communication techniques or a wired connection. Moreover, in some examples, one or more activity sensors may be carried by a therapy delivery element other than a lead, such as a catheter that delivers a therapeutic agent to patient 12.

In the example shown in FIG. 1, a second activity sensor 36 is located within or on outer housing 34 of IMD 16. As with activity sensor 25, activity sensor 36 generates a signal indicative of patient activity, such as patient movement associated with a seizure or a sudden change in patient posture associated with a seizure (e.g., as a result of patient 12 falling down). Activity sensor 36 may include, for example, one or more accelerometers, gyroscopes, pressure transducers, piezoelectric crystals, or other sensors that generate a signal that changes as a function of patient activity. In some cases, an accelerometer may be a single- or multi-axis accelerometer. Because activity sensor 36 is positioned within a torso of patient 12, activity sensor 36 is in a more central location relative to the body of patient 12 than activity sensor 25, which is located in cranium 32 of patient 12.

In some examples, activity sensor 36 may better indicate patient activity that is related to seizures because of the relatively central location. For example, due to the relatively central location, activity sensor 36 may generate a signal that is more indicative of movement of more than one portion of the body of patient 12 than activity sensor 25. In addition, activity sensor 36 may be more sensitive to ripple effects generated by muscle tension in the body of patient 12 because of the location within the torso of patient 12. An ability to detect movement of more than one region of the body of patient 12 may be useful for detecting movement that occurs as a result of motor seizures, which are seizures including a motor component. Thus, due to the more central location of activity sensor 36 relative to the limbs (e.g., arms and legs) and head of patient 12, activity sensor 36 may have the ability to better detect movement of multiple parts of the body of patient 12 resulting from a seizure compared to activity sensor 25 in cranium 32.

Sensor 36 may be more useful for detecting changes in patient posture than sensor 25. Due to the location of sensor 36 within a torso of patient 12, sensor 36 may generate a signal that is more indicative of patient posture than, for example, an activity sensor located within or on an arm, leg or head of patient 12. In particular, an arm, leg or head of patient 12 may be bent relative to the torso, such that the position of the arm, leg or head does not accurately represent the overall patient posture.

In some examples, therapy system 10 includes activity sensor 36 coupled to (e.g., located within or on) housing 34 of IMD 16 and does not include activity sensor 25. However, two or more activity sensors 25, 36 may be useful for determining relative motion between a head of patient 12 and the body of the patient. The relative motion between activity sensors 25, 36 may be detected based on the signals from both activity sensors. In this way, certain patient postures or changes in patient postures may also be discerned based on signals from both activity sensors 25, 36. In some examples, patient activity may also be detected via one or more EMG sensors that generate an electrical signal indicative of muscle movement or one or more intracranial pressure sensor that indicate a change in pressure in cranium 32, which may result from changes in patient posture or a change in patient activity level.

As described in U.S. patent application Ser. Nos. 12/359,037 and 12/359,055 to Giftakis et al., intracranial pressure information may be useful for detecting patient posture transitions. For example, a particular intracranial pressure value may be associated with a particular patient posture in a memory of IMD 16. Thus, a processor may detect a particular intracranial pressure value after detecting a seizure, and determine a patient posture based on the intracranial pressure value. A change in patient posture from a time period preceding the seizure (e.g., a pre-ictal stage) to the time period during or following the seizure may indicate that patient 12 fell during the seizure, which may indicate that the seizure was relatively severe. In this way, intracranial pressure may be useful for distinguishing between severe seizures and relatively minor seizures, whereby severe seizures may be designated target seizures for which therapy delivery is desirable. A relatively severe seizure, e.g., a tonic-clonic seizure, may be characterized by changes in muscle tone and involuntary movements.

Although FIG. 1 illustrates an example of therapy system 10 that includes two activity sensors 25, 36, in other examples, a therapy system may include any suitable number of activity sensors, such as one or more than two. Thus, in other examples, therapy system 10 may include an activity sensor other than or in addition to activity sensors 25, 36. For example, in some examples, therapy system 10 may include an activity sensor carried by a lead that is a separate from leads 20 and electrically connected to IMD 16, or an activity sensor that is physically separate from leads 20 and IMD 16, such as enclosed in a separate outer housing that is implanted within patient 12 or external to patient 12. In examples in which an activity sensor is not implanted within patient 12, the activity sensor may be coupled to patient 12 at any suitable location and via any suitable technique. For example, an accelerometer may be coupled to a leg, torso, wrist, or head of patient 12. In contrast to a physically separate activity sensor, however, activity sensors 25, 36 may provide a more responsive indication of patient movement because activity sensors 25, 36 can be directly electrically connected to a processor of IMD 16 whereas a remote activity sensor may communicate with the processor by wireless telemetry.

IMD 16 implements a seizure detection algorithm to detect seizures of patient 12 based on a first physiological parameter. In the example shown in FIG. 1, the first physiological parameter includes a bioelectrical brain signal, which is sensed via electrodes 24, 26 of leads 20 in the example shown in FIG. 1. A seizure detected based on certain characteristics of a sensed bioelectrical brain signal may be referred to as an electrographic seizure. While many electrographic seizures may occur in brain 28 of patient 12, only some of those electrical seizures may be perceived by patient 12 or determined by the clinician as being severe enough to merit therapy delivery to help mitigate or prevent the occurrence of the seizure. These types of seizures are referred to herein as target seizures.

The physiological manifestations of a target seizure differ between patients and between clinicians, who may determine which seizures are severe enough to merit therapy delivery. In some cases, a target seizure is a seizure that disrupts the daily activities of patient 12, has a lasting physiological impact on patient 12, results in involuntary movement, involuntary body function, changes in behavior, and/or results in a loss of consciousness. For example, a target seizure may be a seizure associated with a motor component (e.g., a tonic-clonic seizure), which may also be referred to as a motor seizure. A motor seizure may place patient 12 in a compromising situation when patient 12 is engaged in certain activities, such as driving. Hence, a target seizure may be a seizure for which delivery of therapy is desirable, i.e., to prevent the seizure, terminate the seizure or alleviate the seizure symptoms.

An electrographic seizure that is not associated with a motor component may be referred to as a sensory seizure. In some cases, patient 12 or a clinician may determine that therapy delivery to manage (e.g., mitigate or prevent) a sensory seizure is not necessary because the sensory seizures do not unduly disrupt the life of the patient. However, in some cases, it may be desirable to deliver electrical stimulation to brain 28 of patient 12 upon detection of a sensory seizure.

It is believed that delivery of electrical stimulation to brain 28 by IMD 16 may help "exercise" the neural circuits of brain 28 and, for example, regulate the electrical activity such that the irregular electrical activity that may result in a seizure is less likely to occur. Thus, delivering stimulation to brain 28 of patient 12 upon detection of a sensory seizure may be useful for providing long term therapy to patient 12. In some examples, therefore, target seizures may include both motor and sensory seizures. In the examples described herein, however, target seizures include motor seizures and do not include sensory seizures, but, rather, include seizures having a physical manifestation of the seizure.

Techniques described herein include monitoring a second patient parameter that is different than the first patient parameter in order to determine which of many sensed electrographic seizures are target seizures for which therapy delivery is desirable. In the example shown in FIG. 1, the second patient parameter includes patient activity sensed via one or both activity sensors 25, 36. In some examples, a processor of IMD 16 may analyze the output from one or both activity sensors 25, 36 to determine a patient activity associated with an electrographic seizure. The patient activity may indicate, for example, the activity level or posture state transition that occurred immediately prior to or during an electrographic seizure. Examples of posture state transitions include, for example, a change in posture from an upright state to a lying down or sitting state.

IMD 16 or programmer 14 may temporally correlate the patient activity information and bioelectrical brain signal information sensed via electrodes 24, 26 in order to determine the one or more brain signal characteristics (also referred to as signal signatures) that are indicative of target seizures. The seizure detection algorithm implemented by IMD 16 may be adjusted or generated with the determined brain signal characteristics, such that IMD 16 is configured to detect the seizure based on the determined brain signal characteristics.

In some examples, patient input provided via programmer 14 may also be correlated with bioelectrical brain signal information in order to identify target seizures. The patient input may indicate that a seizure occurred and therapy delivery for such a seizure is desirable. For example, after the onset of a target seizure, patient 12 may provide input via programmer 14 or IMD 16 (e.g., by tapping IMD 16 in a predetermined pattern, and IMD 16 may include a motion detector to detect the patient input) to indicate a seizure occurred. The input may also indicate a time at which the seizure occurred, such that the patient input may be temporally correlated with the bioelectrical brain signal information. One or more brain signal characteristics that are indicative of the target seizures may be determined by temporally correlating the patient activity information, patient input, and bioelectrical brain signal information. The bioelectrical brain signal characteristics may be the signal characteristics temporally correlated with the patient activity information that is indicative of a target seizure (e.g., an activity level exceeding a threshold level or a sudden posture state transition) and/or the patient input indicative of the onset of the target seizure.

Example systems and techniques for receiving patient input to collect information related to the occurrence of a seizure or a symptom associated with a seizure are described in U.S. patent application Ser. No. 12/236,211 to Kovach et al., entitled, "PATIENT EVENT INFORMATION," which was filed on Sep. 23, 2008 and is incorporated herein by reference in its entirety. As described in U.S. patent application Ser. No. 12/236,211 to Kovach et al., a processor of programmer 14 or another computing device may generate an event marker upon activation of an event indication button of programmer 14 by patient 12. For example, if patient 12 detects an aura associated with a seizure, patient 12 may activate the event indication button, and, in response, the processor may generate an event marker. The patient may provide event information relating to the patient event. For example, the event information may include the type of seizure, severity of seizure, duration of seizure, drug type and dose, a subjective rating of the efficacy of therapy that is delivered to manage the patient's seizure disorder, and the like. Programmer 14 may provide a user interface that is configured to receive the event information from the patient, and, in some examples, may prompt the patient for the information.

Automatically identifying target seizures that have occurred based on a secondary patient parameter that is not the parameter with which IMD 16 detects the seizures to control therapy delivery provides a robust therapy delivery system. Therapy system 10 relies on a primary patient parameter to control therapy delivery, thereby simplifying the seizure detection, but also employs a secondary parameter for determining whether the IMD 16 is properly detecting target seizures. Relying on a primary patient parameter, rather than both the primary and secondary parameters, to control therapy delivery may help reduce the complexity of the computations implemented by IMD 16 to detect a seizure, which may help minimize power consumption by IMD 16.

In some examples, IMD 16 detects the prospective occurrence of the seizure based on the primary patient parameter (e.g., the bioelectrical brain signal) prior to the actual occurrence of physical manifestations of the seizure. In contrast, the secondary patient parameter indicates the actual occurrence of motor components of the seizure. For example, in examples in which the secondary patient parameter comprises patient motion, the secondary parameter can be a relatively reliable indicator of the actual occurrence of a seizure having a motor component. Thus, because IMD 16 may detect the occurrence of a seizure based on the first patient parameter prior to the actual occurrence of physical manifestations of the seizure, the first patient parameter is suitable for driving course of action (e.g., therapy delivery or a warning) in order to either prevent the seizure (e.g., by providing stimulation therapy) or to provide a warning to patient 12 indicating the prospective occurrence of the seizure.

Adjusting the seizure detection algorithm implemented by IMD 16 with the brain signal characteristics that are known to be associated with target seizures may help limit the number of false positive and false negative detections of target seizures by IMD 16. For example, the patient activity information from one or both activity sensors 25, 36 may indicate whether IMD 16 failed to deliver therapy to patient 12 when a target seizure occurred, thereby indicating that the seizure detection algorithm implemented by IMD 16 was not configured to detect the target seizure. In addition, the patient activity information may indicate whether IMD 16 is delivering therapy to patient 12 when an electrographic seizure occurs, but a target seizure does not occur (e.g., because of a lack of a motor component associated with the electrical seizure), thereby indicating the seizure detection algorithm is mischaracterizing some bioelectrical brain signal activity as target seizures.

In addition to updating an existing seizure detection algorithm, the techniques described herein may be used to generate the seizure detection algorithm for IMD 16 during initial programming of the medical device or follow-up programming of the medical device. The techniques described herein may be useful for determining the bioelectrical brain signal characteristics that are indicative of a target seizure.

In some cases, a seizure occurs when the electrical activity within brain 28 of patient 12 exhibits abnormal, excessive or synchronous activity. A clinician may evaluate patient activity level monitored by one or both activity sensors 25, 36 and/or an external activity sensor, as well as the bioelectrical brain signals patient 12 during an evaluation period in order to determine the parameters for the seizure detection algorithm of IMD 16. In some cases, patient input indicating the onset of a target seizure may also be received, as described above. During the course of evaluating patient 12, the clinician may determine, for example, that the bioelectrical brain signal characteristics (e.g., amplitude, slope, pattern, frequency, or frequency band characteristics) indicate an onset of a target seizure for which therapy delivery is desired.

While many electrical seizures may occur in brain 28 of patient 12, only some of those electrical seizures may be perceived by patient 12 or determined by the clinician as being severe enough to merit therapy delivery to help mitigate or prevent the occurrence of the seizure. As described herein, patient activity may be monitored in order to help the clinician determine which of the many sensed electrical seizures are associated with seizures for which therapy delivery is desired. In some cases, a clinician may characterize a seizure associated with a motor component, such as tonic-clonic seizures, as a target seizure that merits therapy delivery. Activity sensors 25, 36 (or an external activity sensor) may be useful for determining which of the many sensed electrical seizures are associated with a motor component. After identifying the electrical signal indicative of a seizure associated with a motor component, the clinician may program IMD 16 to deliver therapy only upon detecting a motor seizure.

Electrical stimulation generated by IMD 16 may be configured to manage a variety of disorders and conditions. In some examples, the stimulation generator of IMD 16 is configured to generate and deliver electrical pulses to patient 12 via electrodes of a selected combination of electrodes 24, 26 (referred to as an "electrode combination"). However, in other examples, the stimulation generator of IMD 16 may be configured to generate and deliver a continuous wave signal, e.g., a sine wave or triangle wave. In either case, a signal generator within IMD 16 may generate the electrical stimulation therapy for DBS according to a therapy program that is selected at that given time in therapy. In examples in which IMD 16 delivers electrical stimulation in the form of stimulation pulses, a therapy program may define values for a set of therapy parameters, such as a stimulation electrode combination for delivering stimulation to patient 12, pulse frequency, pulse width, and a current or voltage amplitude of the pulses. A stimulation electrode combination may indicate the specific electrodes 24, 26 that are selected to deliver stimulation signals to tissue of patient 12 and the respective polarities of the selected electrodes.

In the example shown in FIG. 1, IMD 16 includes a memory to store a plurality of therapy programs that each defines a set of therapy parameter values. In some examples, IMD 16 may select a therapy program from the memory based on various parameters, such as based on one or more characteristics of a bioelectrical brain signal, based on the time of day, and the like. IMD 16 may generate electrical stimulation according to the therapy parameter values defined by the selected therapy program to manage the patient symptoms associated with a seizure disorder.

During a trial stage in which IMD 16 is evaluated to determine whether IMD 16 provides efficacious therapy to patient 12, a plurality of therapy programs may be tested and evaluated for efficacy. Therapy programs may be selected for storage within IMD 16 based on the results of the trial stage. During chronic therapy in which IMD 16 is implanted within patient 12 for delivery of therapy on a non-temporary basis, IMD 16 may generate and deliver stimulation signals to patient 12 according to different therapy programs. In addition, in some examples, patient 12 may modify the value of one or more therapy parameter values within a single given program or switch between programs in order to alter the efficacy of the therapy as perceived by patient 12 with the aid of programmer 14. IMD 16 may store instructions defining the extent to which patient 12 may adjust therapy parameters, switch between programs, or undertake other therapy adjustments. Patient 12 may generate additional programs for use by IMD 16 via external programmer 14 at any time during therapy or as designated by the clinician.

External programmer 14 wirelessly communicates with IMD 16 as needed to provide or retrieve therapy information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. Alternatively, programmer 14 may be a patient programmer that allows patient 12 to select programs and/or view and modify therapy parameters. The clinician programmer may include more programming features than the patient programmer. In other words, more complex or sensitive tasks may only be allowed by the clinician programmer to prevent an untrained patient from making undesired changes to IMD 16.

Programmer 14 may be a handheld computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device or another input mechanism that allows the user to navigate though the user interface of programmer 14 and provide input. If programmer 14 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 14 may be a touch screen that allows the user to provide input directly to the user interface shown on the display. The user may use a stylus or their finger to provide input to the display.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as a secure medical device programmer 14. A wireless adapter coupled to the computing device may enable secure communication between the computing device and IMD 16.

When programmer 14 is configured for use by the clinician, programmer 14 may be used to transmit initial programming information to IMD 16. This initial information may include hardware information, such as the type of leads 20, the arrangement of electrodes 24, 26 on leads 20, the number and location of activity sensors 25, 36 within patient 12, the position of leads 20 within brain 28, the configuration of electrode array 24, 26, initial programs defining therapy parameter values, and any other information the clinician desires to program into IMD 16. Programmer 14 may also be capable of completing functional tests (e.g., measuring the impedance of electrodes 24, 26 of leads 20).

The clinician may also store therapy programs within IMD 16 with the aid of programmer 14. During a programming session, the clinician may determine one or more therapy programs that provide efficacious therapy to patient 12 to address symptoms associated with the seizure disorder. For example, the clinician may select one or more electrode combinations with which stimulation is delivered to brain 28. During the programming session, patient 12 may provide feedback to the clinician as to the efficacy of the specific program being evaluated or the clinician may evaluate the efficacy based on one or more physiological parameters of patient (e.g., heart rate, respiratory rate, or muscle activity). Programmer 14 may assist the clinician in the creation/identification of therapy programs by providing a methodical system for identifying potentially beneficial therapy parameter values.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12. In this manner, programmer 14 may only allow patient 12 to adjust values for certain therapy parameters or set an available range of values for a particular therapy parameter.

Programmer 14 may also provide an indication to patient 12 when therapy is being delivered, when patient input has triggered a change in therapy or when the power source within programmer 14 or IMD 16 needs to be replaced or recharged. For example, programmer 14 may include an alert LED, may flash a message to patient 12 via a programmer display, generate an audible sound or somatosensory cue to confirm patient input was received, e.g., to indicate a patient state or to manually modify a therapy parameter. In addition, programmer 14 may provide a notification to patient 12, a caregiver, and/or a clinician when a seizure is detected by IMD 16. A notification of a likelihood of a seizure may provide patient 12 with sufficient notice to, for example, prepare for the onset of the seizure (e.g., by stopping a vehicle if patient 12 is driving the vehicle). IMD 16 may generate and transmit a signal to programmer 14 upon the detection of the seizure based on the first patient parameter, e.g., the bioelectrical brain signal in the example shown in FIG. 1.

Whether programmer 14 is configured for clinician or patient use, programmer 14 is configured to communicate to IMD 16 and, optionally, another computing device, via wireless communication. Programmer 14, for example, may communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

Therapy system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively long-term treatment.

In addition to or instead of electrical stimulation therapy, IMD 16 may deliver a therapeutic agent to patient 12 to manage a seizure disorder. In such examples, IMD 16 may include a fluid pump or another device that delivers a therapeutic agent in some metered or other desired flow dosage to the therapy site within patient 12 from a reservoir within IMD 16 via a catheter. IMD 16 may deliver the therapeutic agent upon detecting a seizure with a seizure detection algorithm that detects the seizure based on bioelectrical brain signals or another patient parameter. The catheter used to deliver the therapeutic agent to patient 12 may include one or more electrodes for sensing bioelectrical brain signals of patient 12.

Examples of therapeutic agents that IMD 16 may deliver to patient 12 to manage a seizure disorder include, but are not limited to, lorazepam, carbamazepine, oxcarbazepine, valproate, divalproex sodium, acetazolamide, diazepam, phenytoin, phenytoin sodium, felbamate, tiagabine, levetiracetam, clonazepam, lamotrigine, primidone, gabapentin, phenobarbital, topiramate, clorazepate, ethosuximide, and zonisamide. Other therapeutic agents may also provide effective therapy to manage the patient's seizure disorder, e.g., by minimizing the severity, duration, and/or frequency of the patient's seizures. In other examples, IMD 16 may deliver a therapeutic agent to tissue sites within patient 12 other than brain 28.

While the remainder of the disclosure describes various systems, devices, and techniques for adjusting a seizure detection algorithm with respect to therapy system 10 of FIG. 1, the systems, devices, and techniques described herein are also applicable to other types of therapy systems, such as therapy systems that deliver a therapeutic agent to patient 12 to manage a seizure disorder or therapy systems that only provide a notification to patient 12 upon detection of a seizure. In some cases, the therapy system may be used for monitoring bioelectrical brain signals and patient activity of patient 12 and may not include therapy delivery (e.g., stimulation delivery or therapeutic agent delivery) capabilities. The monitoring device may be useful for the clinician during, for example, initial evaluation of patient 12 to generate a seizure detection algorithm.

Figure 2:
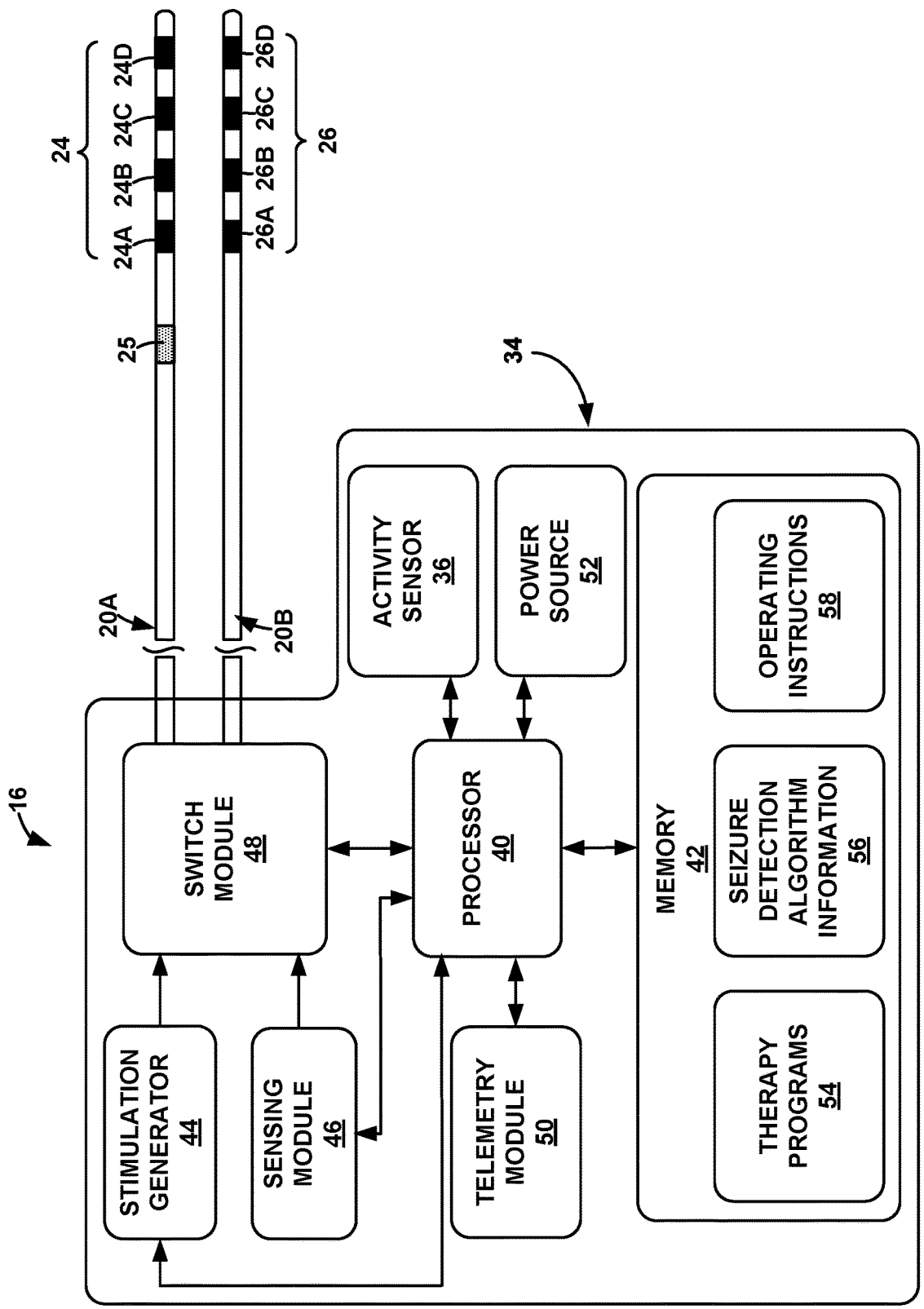
FIG. 2 is functional block diagram illustrating components of an example medical device.

FIG. 2 is a functional block diagram illustrating components of an example IMD 16. In the example shown in FIG. 2, IMD 16 includes activity sensor 36, processor 40, memory 42, stimulation generator 44, sensing module 46, switch module 48, telemetry module 50, and power source 52. Processor 40 may include any one or more microprocessors, controllers, digital signal processors (DSPs), application specific integrated circuits (ASICs), field-programmable gate arrays (FPGAs), discrete logic circuitry. The functions attributed to processors described herein, including processor 40, may be provided by a hardware device and embodied as software, firmware, hardware, or any combination thereof.

In the example shown in FIG. 2, sensing module 46 senses bioelectrical brain signals of patient 12 via select combinations of electrodes 24, 26. Sensing module 46 may include circuitry that measures the electrical activity of a particular region, e.g., an anterior nucleus, thalamus or cortex of brain 28 via select electrodes 24, 26. Sensing module 46 may acquire the bioelectrical brain signal substantially continuously or at regular intervals, such as, but not limited to, at a frequency of about 1 Hz to about 1000 Hz, such as about 250 Hz to about 1000 Hz or about 500 Hz to about 1000 Hz. Sensing module 46 includes circuitry for determining a voltage difference between two electrodes 24, 26, which generally indicates the electrical activity within the particular region of brain 28. One of the electrodes 24, 26 may act as a reference electrode, and, if sensing module 46 is implanted within patient 12, a housing of IMD 16 or the sensing module in examples in which sensing module 46 is separate from IMD 16, may include one or more electrodes that may be used to sense bioelectrical brain signals.

The output of sensing module 46 may be received by processor 40. In some cases, processor 40 may apply additional processing to the bioelectrical signals, e.g., convert the output to digital values for processing and/or amplify the bioelectrical brain signal. In addition, in some examples, sensing module 46 or processor 40 may filter the signal from the selected electrodes 24, 26 in order to remove undesirable artifacts from the signal, such as noise from electrocardiogram signals or EMG signals generated within the body of patient 12. Although sensing module 46 is incorporated into a common outer housing 34 with stimulation generator 44 and processor 40 in FIG. 2, in other examples, sensing module 46 is in a separate outer housing from outer housing 34 of IMD 16 and communicates with processor 40 via wired or wireless communication techniques. In other examples, a bioelectrical brain signal may be sensed via external electrodes (e.g., scalp electrodes).

In some examples, sensing module 46 may not monitor bioelectrical brain signals of patient 12 at substantially the same time that therapy is delivered to patient 12, e.g., because the sense electrodes may be the same as the stimulation electrodes. Thus, in some examples, one or both activity sensors 25, 36 may also be used to determine when a motor seizure has ended, such that sensing module 46 may resume sensing bioelectrical brain signals of patient 12.

Activity sensors 25, 36, which may also be referred to as motion sensors or posture sensors, each generate a signal indicative of patient activity, which may include patient movement and patient posture. The activity signals generated by sensors 25, 36 independently indicate patient activity. As previously indicated, activity sensors 25, 36 each include one or more accelerometers (e.g., single-axis, two-axis or three-axis accelerometers), gyroscopes, pressure transducers, piezoelectric crystals, or other sensors that generate a signal indicative of patient movement. Processor 40 receives the signals generated by activity sensors 25, 36 to determine an activity level of patient 12 or determine whether patient 12 has undergone a posture state transition indicative of a target seizure for which therapy delivery is desirable.

As previously indicated, in some examples, IMD 16 does not include activity sensor 25, while in other examples, IMD 16 does not include activity sensor 36. For ease of description, IMD 16 including activity sensor 36 and not including activity sensor 25 is referenced throughout the remainder of the description.

Processor 40 does not directly control therapy delivery to patient 12 based on signals from activity sensor 36. That is, while processor 40 detects a seizure and subsequently controls stimulation generator 44 to generate and deliver stimulation therapy to patient 12 upon detecting the seizure, processor 40 detects the seizure based on a primary physiological parameter that is not patient activity. In the example shown in FIG. 2, the primary physiological parameter is a bioelectrical brain signal. As described in further detail below, the signal from activity sensor 36 may be used as a secondary parameter that is used to adjust a seizure detection algorithm with which processor 40 detects a target seizure based on the bioelectrical brain signal sensed by sensing module 46. In some cases, activity sensor 36 indicates a target seizure in situations in which the seizure detection algorithm may not detect the target seizure based on the bioelectrical brain signal.

Memory 42 may include any volatile or non-volatile media, such as a random access memory (RAM), read only memory (ROM), non-volatile RAM (NVRAM), electrically erasable programmable ROM (EEPROM), flash memory, and the like. Memory 42 may store computer-readable instructions that, when executed by processor 40, cause IMD 16 to perform various functions described herein.

In the example shown in FIG. 2, memory 42 stores therapy programs 54, seizure detection algorithm information 56, and operating instructions 58 in separate memories within memory 42 or separate areas within memory 42. Each stored therapy program 54 defines a particular program of therapy in terms of respective values for electrical stimulation parameters, such as a stimulation electrode combination, electrode polarity, current or voltage amplitude, and, if stimulation generator 44 generates and delivers stimulation pulses, the therapy programs may define values for a pulse width, pulse rate, and duty cycle of a stimulation signal. In some examples, the therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis. Operating instructions 58 guide general operation of IMD 16 under control of processor 40.

As previously indicated, in some examples, processor 40 detects a seizure based on bioelectrical brain signals sensed by sensing module 46 via a subset of electrodes 24, 26. Seizure detection algorithm information 56 stores the seizure detection algorithm implemented by processor 40 to detect a target seizure. Upon detection of the target seizure, processor 40 controls stimulation generator 44 to deliver therapy to patient 12 or generates a notification to patient 12 (e.g., by causing housing 34 to vibrate or generating another somatosensory notification). In other examples, processor 40 controls programmer 14 or another device to generate a patient notification that alerts patient 12 about the possibility of the seizure onset upon detection of the target seizure based on the bioelectrical brain signal.

In some examples, processor 40 detects a seizure by comparing an amplitude of a sensed bioelectrical brain signal to a threshold value that is stored as part of the seizure detection algorithm in memory 42. The amplitude may be an instantaneous, average, median, lowest or highest amplitude over a predetermined range of time. In one example, when the amplitude of the bioelectrical signal is greater than or equal to the threshold value, processor 40 detects a seizure and controls stimulation generator 44 to generate and deliver therapy to patient 12 via selected electrodes 24, 26.

In other examples, processor 40 detects a seizure by comparing a slope of the time domain bioelectrical brain signal over time or timing between inflection points or other critical points in the pattern of the amplitude of the bioelectrical brain signal over time to trend information. The trend information may be stored as part of the seizure detection algorithm in memory 42. A substantial correlation (e.g., 75% or greater correlation) between the inflection points in the amplitude waveform of the bioelectrical brain signal or other critical points and a template may indicate the onset or a likely onset of a seizure. Seizure detection algorithm information 56 may store an algorithm that recognizes a trend of the bioelectrical brain signal that characterizes a brain state that indicates the onset or the potential onset of the seizure. If the trend of the bioelectrical brain signal matches or substantially matches the trend template, processor 40 detects a seizure and controls stimulation generator 44 to generate and deliver therapy to patient 12 via selected electrodes 24, 26.

As another example, processor 40 may perform temporal correlation by sampling the bioelectrical brain signal with a sliding window and comparing the sampled waveform with a stored template waveform. For example, processor 40 may perform a correlation analysis by moving a window along a digitized plot of the amplitude waveform of bioelectrical brain signal at regular intervals, such as between about one millisecond to about ten millisecond intervals, to define a sample of the bioelectrical brain signal. The sample window is slid along the plot until a correlation is detected between the waveform of the template and the waveform of the sample of the bioelectrical brain signal defined by the window. By moving the window at regular time intervals, multiple sample periods are defined. The correlation may be detected by, for example, matching multiple points between the template waveform and the waveform of the plot of the bioelectrical brain signal over time, or by applying any suitable mathematical correlation algorithm between the sample in the sampling window and a corresponding set of samples stored in the template waveform.

In some examples, processor 40 detects a seizure based on one or more frequency domain characteristics of a bioelectrical brain signal. Either sensing module 46 or processor 40 may tune the bioelectrical brain signal to a particular frequency band that is indicative of the patient's seizure state. The power level within the selected frequency band may be indicative of whether the bioelectrical brain signal indicates patient 12 is in a seizure state. In another example, the ratio of power levels within two or more frequency bands may be compared to a stored value in order to determine whether the bioelectrical brain signal indicates patient 12 is in a seizure state. In another example, the correlation of changes of power between frequency bands may be compared to a stored template to determine whether the bioelectrical brain signal indicates patient 12 is in a seizure state. Thus, in some cases, the algorithm with which processor 40 detects a seizure based on the frequency band characteristics may include a power level within a selected frequency band that is indicative of the seizure state, a ratio of power levels within two or more frequency bands that is indicative of the seizure state, and a relationship between changes in power in two or more frequency bands over time that is indicative of the seizure state.

Seizure detection algorithm information 56 stored by memory 42 may also include bioelectrical brain signals generated by sensing module 46 via selected electrodes 24, 26. In addition, information relating to the patient activity level, as indicated by signals generated by activity sensor 36, may be stored by memory 42 as seizure detection algorithm information 56.

Seizure detection algorithm information 56 also stores instructions with which processor 40 may automatically adjust a seizure detection algorithm, e.g., using techniques described with reference to FIGS. 4-6 and 8. As previously indicated, the seizure detection algorithm implemented by processor 40 to detect a seizure based on a sensed bioelectrical brain signal may be updated based on patient activity information generated by activity sensor 36, bioelectrical brain signal information generated by sensing module 46, and, in some cases, patient input received by IMD 16 or programmer 14 and transmitted to processor 40 of IMD 16.

In some examples, processor 40 automatically adjusts the seizure detection algorithm after analyzing the patient activity information and bioelectrical brain signal, which may be stored as seizure detection algorithm information 56 in memory 42. In other examples, a processor of another device, such as programmer 14 (FIG. 1) may adjust the seizure detection algorithm based on the patient activity information and bioelectrical brain signal generated by IMD 16 and transmitted to the other device.

Processor 40 may adjust the seizure detection algorithm as needed, or at a maximum frequency of about once per hour, once every few hours or once per day or week. Other frequencies for updating the seizure detection algorithm are contemplated. For example, in some cases, processor 40 continuously monitors a signal from activity sensor 36 to determine whether the activity signal is indicative of a target seizure that was not detected based on the bioelectrical brain signal. Processor 40 may adjust the seizure detection algorithm when detecting such a target seizure.

In some cases, processor 40 adjusts a seizure detection algorithm to be more sensitive, e.g., because IMD 16 is failing to deliver therapy to patient 12 when a target seizure occurs. As described in further detail with respect to FIG. 5, in order to update a seizure detection algorithm of IMD 16, processor 40 may use the signal from activity sensor 36 to identify a target seizure that was not based on the bioelectrical signal.

During a target seizure, which may be, for example, an electrographic seizure that is associated with a motor component, patient 12 may undergo movement, e.g., a repetitive, involuntary motion or a sudden change in patient posture, that is characteristic of a seizure rather than other patient motions (e.g., day-to-day activities such as walking, running, riding in a car, and the like). A clinician may store the signal from activity sensor 36 that is indicative of the target seizure motion (e.g., a repetitive motion or a complex motor movement) or patient posture change indicative of the target seizure in memory 42 for use as a template or threshold for detecting target seizures based on the signal from activity sensor 36.

In some examples, the signal from activity sensor 36 may be indicative of a seizure if, for example, a mean, median, instantaneous amplitude, highest or lowest amplitude of the signal within a predetermined period of time is greater than a threshold value stored in memory 42. In other examples, the signal from activity sensor 36 may be indicative of a seizure if the pattern (e.g., slope or timing between inflection points) of the time domain activity sensor signal substantially correlates to a template stored in memory 42. In yet other examples, the signal from activity sensor 36 may be indicative of a seizure if one or more frequency band characteristics has a known relationship (e.g., greater than, less than or equal to) a stored value.

After identifying a target seizure based on the patient activity signal from activity sensor 36, processor 40 may determine whether the seizure detection algorithm is configured such that processor 40 identified the target seizure based on the bioelectrical brain signal. If the target seizure was not identified based on the bioelectrical brain signal, processor 40 may determine the bioelectrical brain signal characteristic indicative of the particular target seizure that was missed by the seizure detection algorithm.

In some examples, prior to identifying the target seizure, processor 40 may determine whether a temporally correlated bioelectrical brain signal exhibited abnormal behavior (e.g., as compared to a baseline state). While the seizure detection algorithm may not be configured to recognize the specific characteristics of the abnormal bioelectrical brain signal as a target seizure, processor 40 may still generally determine whether the bioelectrical brain signal indicates abnormal attributes compared to a baseline non-seizure state. The determination of whether the brain signal generally exhibited abnormal behavior compared to a baseline non-seizure state may be used to confirm that the target seizure detected based on the patient activity signal was in fact attributable to a seizure rather than another patient activity, such as a fall unrelated to the occurrence of a seizure. If, for example, the bioelectrical brain signal indicates the brain activity of patient 12 was normal (e.g., associated with a non-seizure state), processor 40 may determine that the target seizure identified based on the patient activity signal was not an actual seizure.

A "normal" bioelectrical brain signal may be indicated by one or more signal characteristics (e.g., an amplitude or frequency) of the brain signal. The signal characteristics may be determined when patient 12 is known to be in a non-seizure state. This non-seizure state may also be referred to as a baseline state. In some examples, the baseline bioelectrical brain signal characteristic indicative of a non-seizure state may be specific to patient 12, while in other examples, the baseline signal characteristic may be general to a plurality of patients.

After identifying a target seizure based on the patient activity signal, and, in some cases, confirming that the correlated bioelectrical brain signal exhibited abnormal behavior, processor 40 may update the seizure detection algorithm based on the patient activity signal. Processor 40 may determine the bioelectrical brain signal characteristic associated with the target seizure and store the determined bioelectrical brain signal characteristic as part of the seizure detection algorithm. In this way, processor 40 may automatically update a seizure detection algorithm to detect similar target seizures based on monitored patient activity.

In other examples, processor 40 may update a seizure detection algorithm to be less sensitive. For example, processor 40 may also determine that, based on the temporally correlated bioelectrical brain signal and activity sensor signal, the seizure detection algorithm is mischaracterizing non-target seizures as target seizures, resulting in potentially unnecessary therapy delivery to patient 12. Processor 40 may determine whether it is desirable for the seizure detection algorithm to be adjusted to be less sensitive, e.g., because the seizure detection algorithm is identifying electrographic seizures as target seizures when the electrographic seizures are not in fact target seizures for which therapy delivery is desirable.

Figure 6:
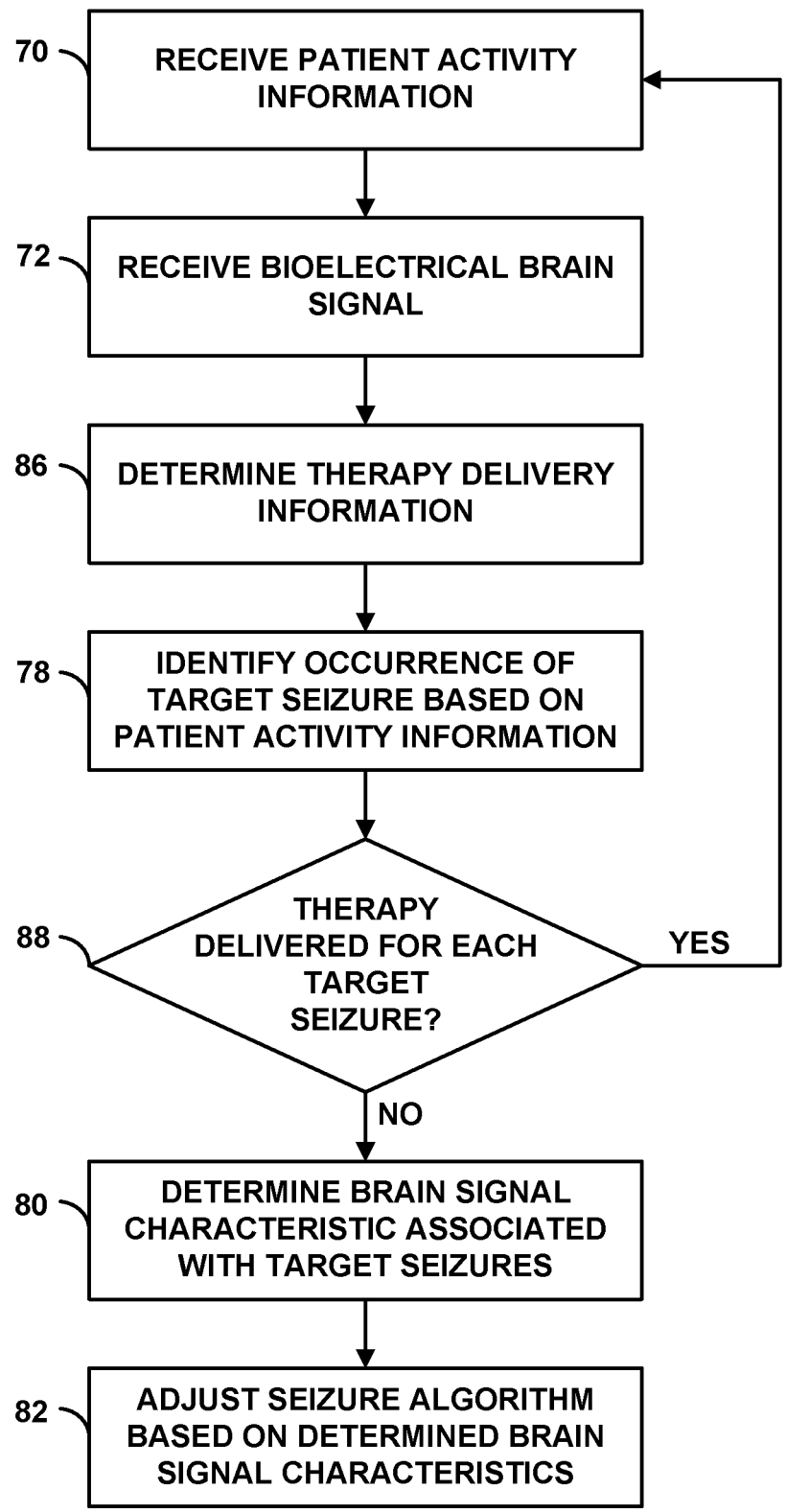
FIG. 6 is a flow diagram of an example technique for adjusting a seizure detection algorithm to minimize the number of false negative target seizure detections.

As described in further detail with respect to FIG. 6, processor 40 may identify when processor 40 detected a target seizure using the current seizure detection algorithm and controlled stimulation generator 44 to deliver therapy to patient 12 upon detection of the target seizure. Processor 40 may determine whether the patient activity signal from activity sensor 36 indicated the detected target seizures were actual target seizures. If the processor 40 detected a seizure that was not a target seizure using the current seizure detection algorithm, thereby resulting in potentially unnecessary therapy to patient 12, processor 40 may determine that the seizure detection algorithm needs to be adjusted to be less sensitive. Processor 40 may then adjust the seizure detection algorithm accordingly. For example, processor 40 may determine which bioelectrical brain signal characteristic triggered the detection of a non-target seizure that resulted in therapy delivery and remove that bioelectrical brain signal characteristic from the seizure detection algorithm.

In some cases, it may be desirable to limit the delivery of unnecessary electrical stimulation to brain 28 of patient 12. Unnecessary electrical stimulation may be, for example, stimulation that is delivered to brain 28 when a target seizure does not occur, e.g., when a purely electrographic seizure without a motor component occurs. It has been found that patient 12 may adapt to deep brain stimulation provided by IMD 16 over time. That is, a certain level of electrical stimulation provided to brain 28 may be less effective over time. This phenomenon may be referred to as "adaptation." As a result, any beneficial effects to patient 12 from the deep brain stimulation may decrease over time. While the electrical stimulation levels (e.g., amplitude of the electrical stimulation signal) may be increased to overcome such adaptation, the increase in stimulation levels may consume more power, and may eventually reach undesirable or harmful levels of stimulation.

When stimulation is provided to manage target seizures rather than all electrographic seizures, which may be frequent, the rate at which patient adaptation to the therapy, whether electrical stimulation, drug delivery or otherwise, may occur may decrease. Thus, automatic adjustment to a seizure detection algorithm implemented by IMD 16 based on patient activity and bioelectrical brain signals enables the therapy provided to patient 12 via IMD 16 to be more effective for a longer period of time as compared to systems in which a seizure detection algorithm is not updated based on detection of target seizures based on correlation of bioelectrical brain signals with patient activity information.

In some cases, it may be desirable to continue the delivery of electrical stimulation to brain 28 of patient 12, despite the mischaracterization of some electrographic seizures as target seizures. As previously indicated it is believed that electrical stimulation to brain 28 may help "exercise" the neural circuits of brain 28 to help reduce the occurrence of abnormal electrical activity that may result in a seizure. Thus, delivering stimulation to brain 28 of patient 12 upon detection of a non-target seizure may be useful for providing long term therapy to patient 12. In some examples, however, the clinician may configure the seizure detection algorithm to be generous in the characterization of target seizures, and, therefore, processor 40 may continue to adjust the seizure detection algorithm in the manner discussed above to be more discerning of target seizures while still maintaining the benefits of the neural circuit exercising.

Stimulation generator 44, under the control of processor 40, generates stimulation signals for delivery to patient 12 via selected combinations of electrodes 24, 26. Processor 40 controls stimulation generator 44 according to therapy programs 54 stored in memory 42 to apply particular stimulation parameter values specified by one or more programs, such as amplitude, pulse width, and pulse rate. In some examples, stimulation generator 44 generates and delivers stimulation signals to anterior nucleus of the thalamus of brain 28 (FIG. 1) of patient 12 via a select combination of electrodes 24, 26, where the stimulation signals have a frequency in a range of about 3 Hertz (Hz) to about 250 Hz, a voltage of about 0.1 volts to about 10.5 volts, and a pulse width of about 60 microseconds to about 450 microseconds. In some examples, the stimulation signals have a frequency of 120 Hz, a voltage of about 4 volts, and a pulse width of about 100 microseconds. In addition, in some examples, the stimulation signals have a frequency of 145 Hz, a voltage of about 5 volts, and a pulse width of about 145 microseconds. In addition, the stimulation signals may have any suitable therapy cycle, which includes an on-cycle during which therapy is delivered to patient 12 and an off-cycle during which therapy is not delivered to patient 12. For example, a therapy cycle may have an on-cycle of about thirty seconds to about five minutes (e.g., about one minute) and an off-cycle of about thirty seconds to about five minutes (e.g., about five minutes).

Other stimulation targets within brain 28, other stimulation parameter values, and other therapy cycles are contemplated. Other ranges of therapy parameter values may also be useful, and may depend on the target stimulation site within patient 12, which may or may not be within brain 28. While stimulation pulses are described, stimulation signals may be of any form, such as continuous-time signals (e.g., sine waves) or the like.

In each of the examples described herein, if stimulation generator 44 shifts the delivery of stimulation energy between two therapy programs and/or two different electrode combinations, processor 40 of IMD 16 may provide instructions that cause stimulation generator 44 to time-interleave stimulation energy between the electrode combinations of the two therapy programs, as described in commonly-assigned U.S. patent application Ser. No. 11/401,100 by Steven Goetz et al., entitled, "SHIFTING BETWEEN ELECTRODE COMBINATIONS IN ELECTRICAL STIMULATION DEVICE," and filed on Apr. 10, 2006, the entire content of which is incorporated herein by reference. In the time-interleaved shifting example, the amplitudes of the stimulation signals delivered via the electrode combinations of the first and second therapy program are ramped downward and upward, respectively, in incremental steps until the amplitude of the second electrode combination reaches a target amplitude. The incremental steps may be different between ramping downward or ramping upward. The incremental steps in amplitude can be of a fixed size or may vary, e.g., according to an exponential, logarithmic or other algorithmic change. When the second electrode combination reaches its target amplitude, or possibly before, the first electrode combination can be shut off. Other techniques for shifting the delivery of stimulation signals between two therapy programs and/or electrode combinations may be used in other examples.

In the example shown in FIG. 2, the set of electrodes 24 of lead 20A includes electrodes 24A, 24B, 24C, and 24D, and the set of electrodes 26 of lead 20B includes electrodes 26A, 26B, 26C, and 26D. Processor 40 may control switch module 48 to apply the stimulation signals generated by stimulation generator 44 to selected combinations of electrodes 24, 26. In particular, switch module 48 may couple stimulation signals to selected conductors within leads 20, which, in turn, deliver the stimulation signals across selected electrodes 24, 26. Switch module 48 may be a switch array, switch matrix, multiplexer, or any other type of switching module configured to selectively couple stimulation energy to selected electrodes 24, 26 and to selectively sense bioelectrical brain signals with selected electrodes 24, 26. Hence, stimulation generator 44 is coupled to electrodes 24, 26 via switch module 48 and conductors within leads 20. In some examples, however, IMD 16 does not include switch module 48.

Stimulation generator 44 may be a single channel or multi-channel stimulation generator. In particular, stimulation generator 44 may be capable of delivering, a single stimulation pulse, multiple stimulation pulses or continuous signal at a given time via a single electrode combination or multiple stimulation pulses at a given time via multiple electrode combinations. In some examples, however, stimulation generator 44 and switch module 48 may be configured to deliver multiple channels on a time-interleaved basis. For example, switch module 48 may serve to time divide the output of stimulation generator 44 across different electrode combinations at different times to deliver multiple programs or channels of stimulation energy to patient 12.

Sensing module 46 is configured to sense bioelectrical brain signals of patient 12 via a selected subset of electrodes 24, 26. Processor 40 may control switch module 48 to electrically connect sensing module 46 to selected combinations of electrodes 24, 26. In this way, sensing module 46 may selectively sense bioelectrical brain signals with different combinations of electrodes 24, 26. As previously described, in some examples, processor 40 may detect a seizure of patient 12 via the sensed bioelectrical brain signal.

Telemetry module 50 supports wireless communication between IMD 16 and an external programmer 14 or another computing device under the control of processor 40. Processor 40 of IMD 16 may receive, as updates to programs, values for various stimulation parameters such as amplitude and electrode combination, from programmer 14 via telemetry module 50. The updates to the therapy programs may be stored within therapy programs 54 portion of memory 42. Telemetry module 50 in IMD 16, as well as telemetry modules in other devices and systems described herein, such as programmer 14, may accomplish communication by radiofrequency (RF) communication techniques. In addition, telemetry module 50 may communicate with external medical device programmer 14 via proximal inductive interaction of IMD 16 with programmer 14. Accordingly, telemetry module 50 may send information to external programmer 14 on a continuous basis, at periodic intervals, or upon request from IMD 16 or programmer 14. For example, processor 40 may transmit seizure detection algorithm information 56 to programmer 14 via telemetry module 50.

Power source 52 delivers operating power to various components of IMD 16. Power source 52 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Figure 3:
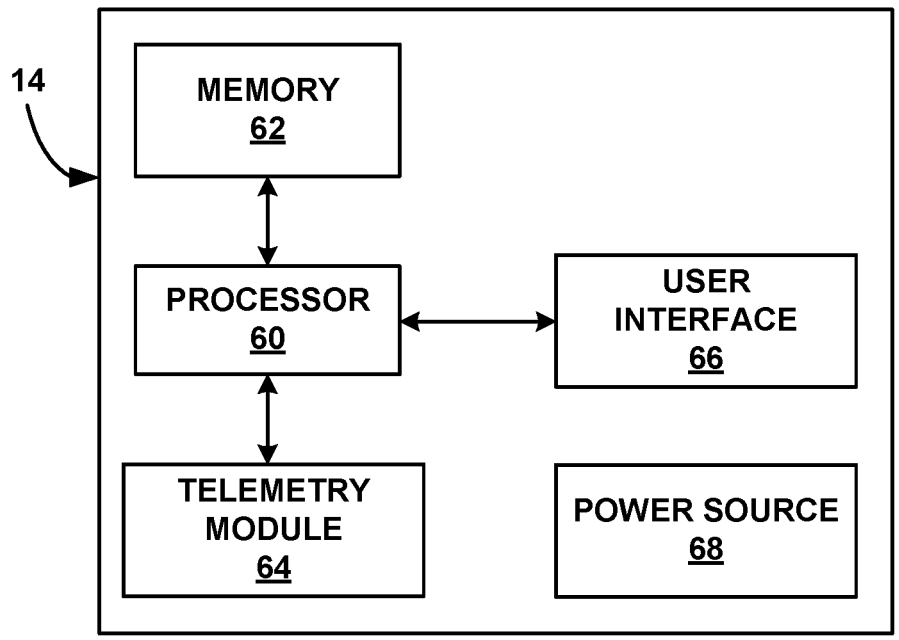
FIG. 3 is a functional block diagram illustrating components of an example medical device programmer.

FIG. 3 is a conceptual block diagram of an example external medical device programmer 14, which includes processor 60, memory 62, telemetry module 64, user interface 66, and power source 68. Processor 60 controls user interface 66 and telemetry module 64, and stores and retrieves information and instructions to and from memory 62. Programmer 14 may be configured for use as a clinician programmer or a patient programmer. Processor 60 may comprise any combination of one or more processors including one or more microprocessors, DSPs, ASICs, FPGAs, or other equivalent integrated or discrete logic circuitry. Accordingly, processor 60 may include any suitable structure, whether in hardware, software, firmware, or any combination thereof, to perform the functions ascribed herein to processor 60.

A user, such as a clinician or patient 12, may interact with programmer 14 through user interface 66. User interface 66 includes a display (not shown), such as a LCD or LED display or other type of screen, to present information related to the therapy, such as information related to bioelectrical signals sensed via a plurality of sense electrode combinations. The display may also be used to present a visual alert to patient 12 that IMD 16 has detected a seizure is about to occur. Other types of alerts are contemplated, such as audible alerts or somatosensory alerts. User interface 66 may also include an input mechanism to receive input from the user. The input mechanisms may include, for example, buttons, a keypad (e.g., an alphanumeric keypad), a peripheral pointing device or another input mechanism that allows the user to navigate though user interfaces presented by processor 60 of programmer 14 and provide input.

If programmer 14 includes buttons and a keypad, the buttons may be dedicated to performing a certain function, i.e., a power button, or the buttons and the keypad may be soft keys that change function depending upon the section of the user interface currently viewed by the user. Alternatively, the screen (not shown) of programmer 14 may be a touch screen that allows the user to provide input directly to the user interface shown on the display. The user may use a stylus or their finger to provide input to the display. In other examples, user interface 66 also includes audio circuitry for providing audible instructions or notifications to patient 12 and/or receiving voice commands from patient 12, which may be useful if patient 12 has limited motor functions. Patient 12, a clinician or another user may also interact with programmer 14 to manually select therapy programs, generate new therapy programs, modify therapy programs through individual or global adjustments, and transmit the new programs to IMD 16.

In some examples, at least some of the control of therapy delivery by IMD 16 may be implemented by processor 60 of programmer 14. For example, in some examples, processor 60 may receive patient activity information and bioelectrical brain signals from IMD 16 or from a sensing module that is separate from IMD 16. The separate sensing module may, but need not be, implanted within patient 12. In some examples, processor 60 may evaluate the patient activity information and bioelectrical brain signals from IMD 16 and adjust a seizure detection algorithm of IMD 16 based on the patient activity information correlated with the bioelectrical brain signals.

In addition, in some examples, a clinician, with the aid of programmer 14, may determine one or more brain signal characteristics indicative of target seizures of patient 12 based on the patient activity information and bioelectrical brain signals generated by IMD 16. Programmer 14 or a clinician with the aid of programmer 14 may generate a seizure detection algorithm based on the determined brain signal characteristics indicative of the target seizures of patient 12.

Memory 62 may include instructions for operating user interface 66 and telemetry module 64, and for managing power source 68. Memory 62 may also store any therapy data retrieved from IMD 16 during the course of therapy, as well as seizure data (e.g., seizure indications that indicate the time and date of a seizure), sensed bioelectrical brain signals, and activity sensor information. The clinician may use this therapy data to determine the progression of the patient condition in order to plan future treatment for the seizure disorder of patient 12. Memory 62 may include any volatile or nonvolatile memory, such as RAM, ROM, EEPROM or flash memory. Memory 62 may also include a removable memory portion that may be used to provide memory updates or increases in memory capacities. A removable memory may also allow sensitive patient data to be removed before programmer 14 is used by a different patient.

Wireless telemetry in programmer 14 may be accomplished by RF communication or proximal inductive interaction of external programmer 14 with IMD 16. This wireless communication is possible through the use of telemetry module 64. Accordingly, telemetry module 64 may be similar to the telemetry module contained within IMD 16. In alternative examples, programmer 14 may be capable of infrared communication or direct communication through a wired connection. In this manner, other external devices may be capable of communicating with programmer 14 without needing to establish a secure wireless connection.

Power source 68 delivers operating power to the components of programmer 14. Power source 68 may include a battery and a power generation circuit to produce the operating power. In some examples, the battery may be rechargeable to allow extended operation. Recharging may be accomplished by electrically coupling power source 68 to a cradle or plug that is connected to an alternating current (AC) outlet. In addition, recharging may be accomplished through proximal inductive interaction between an external charger and an inductive charging coil within programmer 14. In other examples, traditional batteries (e.g., nickel cadmium or lithium ion batteries) may be used. In addition, programmer 14 may be directly coupled to an alternating current outlet to obtain operating power. Power source 68 may include circuitry to monitor power remaining within a battery. In this manner, user interface 66 may provide a current battery level indicator or low battery level indicator when the battery needs to be replaced or recharged. In some cases, power source 68 may be capable of estimating the remaining time of operation using the current battery.

Figure 4:
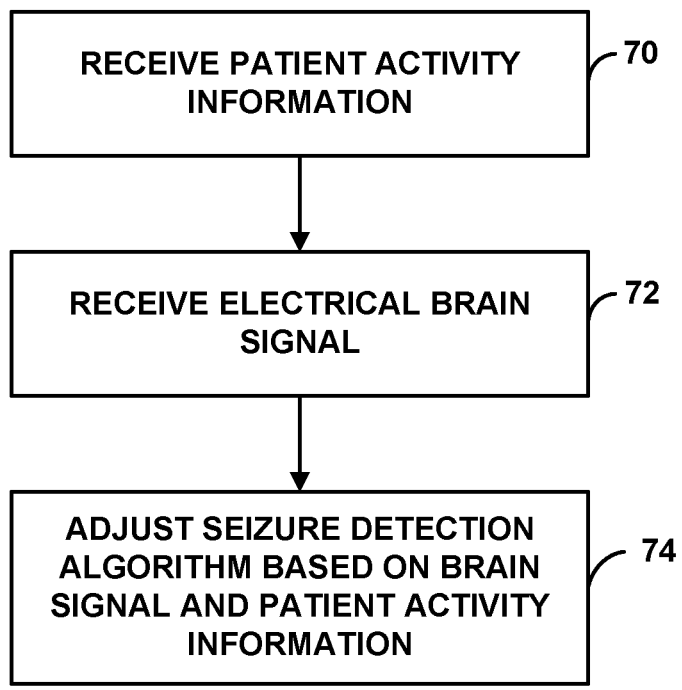
FIG. 4 is a flow diagram of an example technique for adjusting a seizure detection algorithm of a medical device based on different patient parameters.

FIG. 4 is a flow diagram illustrating an example technique that processor 40 (FIG. 2) of IMD 16, processor 60 (FIG. 3) of programmer 14, or a processor of another device may implement in order to adjust a seizure detection algorithm of IMD 16. The techniques described with respect to FIGS. 4-6, 8, and 9 are described as being performed by processor 40. In other examples, however, processor 60 (FIG. 3) of programmer 14, or a processor of another device may implement the techniques described herein.

In accordance with the technique shown in FIG. 4, processor 40 of IMD 16 receives a signal from activity sensor 36 that is indicative of physical patient activity (e.g., patient motion or posture) (70) and receives a bioelectrical brain signal from sensing module 46 that is indicative of electrical activity of brain 28 of patient 12 (72). Processor 40 may continuously receive the signals from activity sensor 36 and sensing module 46 or periodically receive the signals.

Figure 5:
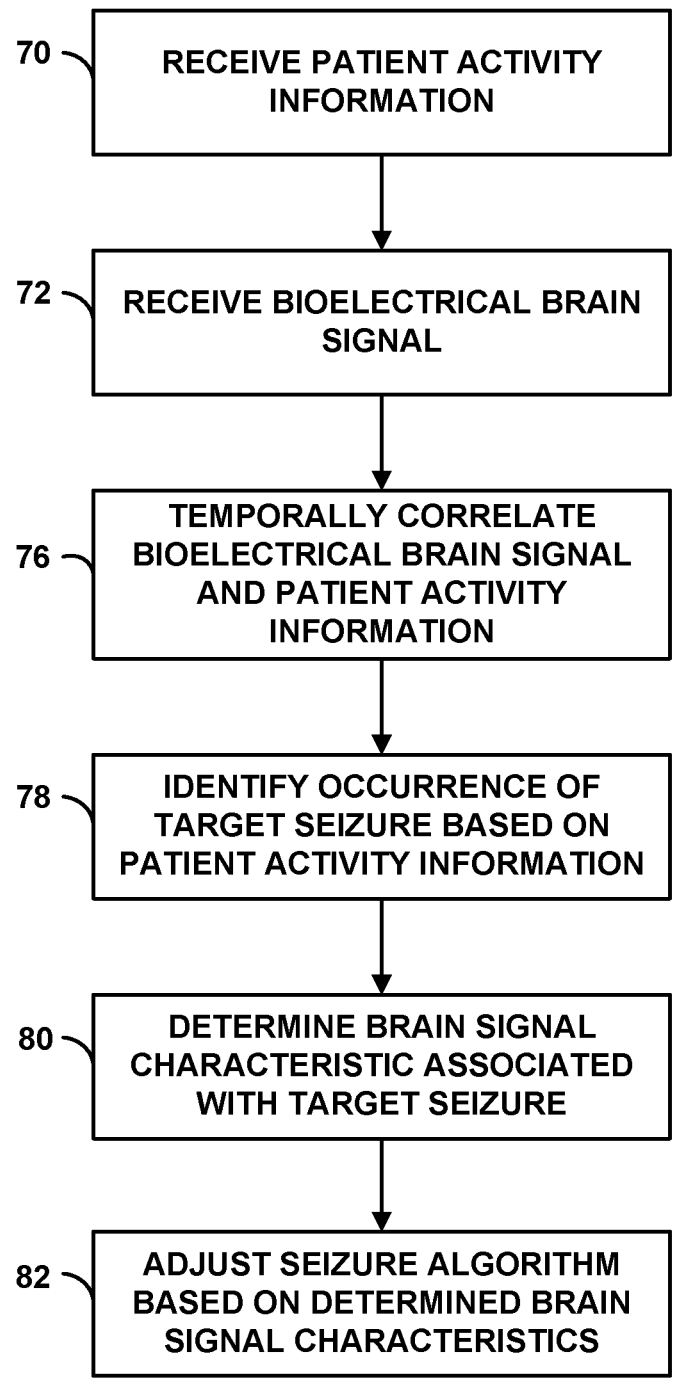
FIG. 5 is a flow diagram of an example technique for adjusting a seizure detection algorithm.

Processor 40 adjusts the seizure detection algorithm based on the patient activity information (indicated by the signal from sensor 36) and the bioelectrical brain signal (74). FIG. 5 illustrates an example technique processor 40 may implement to adjust seizure detection algorithm. After receiving patient activity information (70) from activity sensor 36 and receiving the bioelectrical brain signal (72) from sensing module 46 of IMD 16, processor 40 may temporally correlate the patient activity signal and the bioelectrical brain signal (76).

Processor may identify the occurrence of target seizures based on the patient activity signal (78), and, in some cases, based on patient input indicating the occurrence of a target seizure. A technique for identifying the occurrence of target seizures based on the patient activity signal is described with respect to FIG. 9. A clinician may determine the one or more signal characteristics of the patient activity signal generated by activity sensor 36 that are indicative of a target seizure and store the signal characteristics in memory 42 of IMD 16. For example, the clinician may observe patient 12, e.g., based on video data, or receive patient input to identify the occurrence of a target seizure, and determine which patient activity signal characteristics substantially correspond to the occurrence of the target seizure. The one or more patient activity signal characteristics may then be stored in memory 42 of IMD 16.

In some cases, the one or more activity signal characteristics indicative of a target seizure include a threshold amplitude, whereby if the mean, median, instantaneous, highest or lowest amplitude of the patient activity signal during a predefined range of time is greater than or equal to the threshold amplitude, processor 40 determines that the target seizure occurred. In other examples, the one or more activity signal characteristics include a signal template, whereby if the patient activity signal substantially correlates with the signal template (e.g., the slope or timing between inflection points), processor 40 determines that the target seizure occurred.

Other types of patient activity signal characteristics indicative of a target seizure are contemplated. For example, in some cases, the one or more activity signal characteristics indicative of a target seizure are not predetermined and stored in IMD 16, but, rather, processor 40 determines whether the activity signal indicates a sudden increase in patient activity level (e.g., as indicated by a slope exceeding a stored threshold) or a sudden change in patient posture. The sudden increase in patient activity level or change in patient posture may indicate the occurrence of a target seizure, particularly in examples in which the target seizure is a motor seizure with associated involuntary movement.

Processor 40 may implement any suitable statistical analysis to determine whether the patient activity signal is indicative of a target seizure. In some examples, processor 40 determines whether the patient activity signal has a relatively low variance, e.g., by comparing a statistical metric (e.g., a mean, median, lowest or highest amplitude value) for a current time period to the statistical metric for previous time periods. If the statistical metric for the current time period is within a threshold range of the statistical metric for the previous time periods, processor 40 may determine that the patient activity level is not indicative of a target seizure. However, if the statistical metric for the current time period falls outside of the threshold range of the statistical metrics for the previous time periods, processor 40 may determine that the patient activity signal is indicative of a sudden posture change or a sudden increase in activity, which may be indicative of a target seizure.

Processor 40 may also remove portions of the patient activity signal that correspond to a known activity of patient (e.g., walking to work), which are activities known to occur on a regular basis. For example, processor 40 may store the patient activity signal that corresponds to the known activity of patient 12 and compare the signal from activity sensor 36 to determine whether a detected increase in patient activity is attributable to a benign patient activity rather than a target seizure.

In some examples, processor 40 confirms that the target seizure that was identified based on the patient activity signal was an actual seizure before adjusting a seizure detection algorithm. For example, processor 40 may determine whether the bioelectrical brain signal temporally correlated with the target seizure that was identified based on the patient activity signal exhibited abnormal behavior (e.g., as compared to a baseline state). If processor 40 determines that one or more characteristics (e.g., amplitude or frequency) of the bioelectrical brain signal indicates the brain activity of patient 12 during the target seizure was similar to a characteristic during a non-seizure state, processor 40 may determine that the target seizure identified based on the patient activity signal was not an actual target seizure. In some cases, the activity signal may indicate a patient activity that is unrelated to the occurrence of a target seizure. Thus, by determining whether the bioelectrical brain signal suggests a seizure may have occurred, e.g., by comparing the brain signal to a baseline non-seizure state, processor 40 can confirm that the target seizure identified based on the patient activity was a true seizure.

After identifying a target seizure based on the patient activity signal, and, in some cases, confirming that the correlated bioelectrical brain signal exhibited abnormal behavior, processor 40 may update the seizure detection algorithm based on the patient activity signal. In the technique shown in FIG. 5, processor 40 selects the bioelectrical brain signal corresponding to the patient activity signal that is indicative of the target seizure to determine the bioelectrical brain signal characteristic indicative of the target seizure identified based on the patient motion information (80). In order to help distinguish between target and non-target seizures, for which therapy delivery is not desirable or necessary, processor 40 may select the bioelectrical brain signal characteristic that is different than the brain signal characteristics exhibited by brain 28 during a non-target seizure.

In some cases, processor 40 determines the one or more characteristics of the bioelectrical brain signal temporally correlating to the target seizure. The brain signal characteristics indicative of a seizure may include, for example, a mean, median, highest or lowest amplitude of a period of time preceding or overlapping with the time of occurrence of the target seizure, an instantaneous amplitude, one or more frequency band characteristics of the bioelectrical brain signal preceding or overlapping with the time of occurrence of the target seizure, or a signal template generated based on the bioelectrical brain signal sensed during the time period preceding the or overlapping with the time of occurrence of the target seizure. Other types of brain signal characteristics that may be determined based on the bioelectrical brain signal corresponding to the patient activity signal that is indicative of the target seizure are contemplated.

As previously indicated, processor 40 may identify the occurrence of target seizures based on one or more patient parameters other than or in addition to patient activity. Thus, while the technique shown in FIGS. 4-6, 8, and 9 are described with respect to patient activity, in other examples, processor 40 may determine bioelectrical brain signal characteristics indicative of a target seizure by correlating a sensed bioelectrical brain signal with a heart rate signal, respiration rate signal, intracranial pressure signal, muscle activity (e.g., EMG) signal, and the like. As previously indicated, sudden changes in heart rate signal, respiration rate signal, intracranial pressure signal, or muscle activity signal or a heart rate, respiration rate, intracranial pressure or muscle activity level that exceeds a threshold value or substantially correlates to a stored template may be indicative of an occurrence of a target seizure. Thus, processor 40 may implement techniques similar to those described with respect to a patient activity signal to identify the occurrence of target seizures based on a heart rate signal, respiration rate signal, intracranial pressure signal, or muscle activity signal.

After processor 40 determines the bioelectrical brain signal characteristics associated with target seizures, processor 40 may adjust the seizure detection algorithm based on the determined bioelectrical brain signal characteristics (82). For example, processor 40 may store the determined bioelectrical brain signal characteristics as seizure detection algorithm information 56 (FIG. 2), such that the detection of the one or more determined bioelectrical brain signal characteristics in the future will result in detection of a target seizure.

As previously indicated, processor 40 may also determine the one or more characteristics of the bioelectrical brain signal temporally correlating to the target seizure based on patient input in addition to patient activity information. The patient input that indicates whether a target seizure was experienced by patient 12 may provide an additional layer of information that helps generate a useful seizure detection algorithm. For example, in some cases, the patient activity signal generated by activity sensor 36 may indicate the occurrence of a target seizure, but patient 12 may not have provided input indicating the occurrence of the target seizure within a predetermined time of detecting the target seizure. Processor 40 may determine that the target seizure identified based on the patient activity signal is not a seizure that bothered patient 12, and, therefore, processor 40 may decategorize the seizure as a target seizure. That is, if patient 12 fails to indicate that a seizure detected based on the patient activity signal occurred, processor 40 may not adjust the seizure detection algorithm based on the detected seizure.

In some cases, processor 40 also determines whether patient 12 provided input indicating that a detected seizure (e.g., a notification can be presented to patient 12 via programmer 14) was not a target seizure, and if the patient input is not received within a predetermined amount of time, processor 40 determines the target seizure was a true seizure. However, in some examples, patient 12 may not have provided input because of a lack of access to programmer 14 or because of an oversight. Thus, in some examples, processor 40 may determine the one or more bioelectrical brain signal characteristics associated with the target seizure identified based on the patient activity signal, and adjust the seizure detection algorithm (82) despite the absence of patient input associated with the target seizure.

The technique shown in FIG. 5 may also be implemented by programmer 14 or a clinician, alone or with the aid of programmer 14, to generate a seizure detection algorithm that is used by IMD 16 for therapy delivery. Determining the one or more bioelectrical brain signal characteristics that are indicative of electrographic seizures may not be meaningful enough to generate a seizure detection algorithm that provides useful seizure disorder therapy to patient 12. Moreover, while bioelectrical brain signals may indicate the occurrence of an electrographic seizure, the one or more characteristics of the bioelectrical brain signal that are indicative of a target seizure (e.g., a motor seizure) may not be easily discernable. For example, while video or other visual monitoring of patient 12 may indicate which electrographic seizures are associated with a motor component, such visual monitoring of patient 12 may be burdensome for both patient 12 and the clinician, e.g., because of the investment of time required to observe one or more motor seizures. In addition, the manual review of stored bioelectrical signal information and patient observation information to determine the one or more the bioelectrical brain signal characteristics that are indicative of a target seizure may be overwhelming and inefficient for a clinician because of the large volume of information.

The technique shown in FIG. 5 may be implemented during programming of IMD 16, e.g., upon initial implantation of IMD 16 or during follow-up programming of IMD 16 after IMD 16 has delivered therapy to patient 12 for a while, to generate a seizure detection algorithm that discerns between electrographic seizures for which seizure disorder therapy is desirable and electrographic seizures for which seizure disorder therapy is not necessary or desirable. Patient activity information provided by activity sensor 36 helps a clinician or programmer 14 determine the brain signal characteristics that are indicative of target seizures without requiring long-term visual observation of patient 12. IMD 16 may collect the patient activity signal over a period of time (e.g., days or even weeks or more) to generate the information necessary to determine the brain signal characteristics that are indicative of target seizures in accordance with the technique shown in FIG. 4.

In some examples, programmer 14 or IMD 16 may automatically determine the one or more brain signal characteristics that are indicative of target seizures, thereby eliminating the need for a clinician to manually review the relevant information. In addition, an automated technique for determining the one or more brain signal characteristics that are indicative of target seizures may help reduce human error.

As previously indicated, in some examples, processor 40 adjusts the seizure detection algorithm to reduce the number of false negative seizure detections. FIG. 6 is a flow diagram illustrating an example technique with which processor 40 may adjust a seizure detection algorithm upon determining that the seizure detection algorithm is mischaracterizing seizures as non-target seizure, such that IMD 16 is not sensitive enough to target seizures. As with the technique shown in FIG. 5, processor 40 receives patient activity information, e.g., by receiving a signal from activity sensor 36 (70) and receives a bioelectrical brain signal from sensing module 46 (FIG. 2) (72).

Processor 40 determines information relating to when therapy was delivered to patient 12 (therapy delivery information) (86). In the example shown in FIG. 6, processor 40 determines when target seizures were detected based on bioelectrical brain signals while processor 40 was implementing the current seizure detection algorithm, and, thus, when processor 40 controlled stimulation generator 44 to generate and deliver electrical stimulation therapy to patient 12. In other examples, processor 40 may determine when stimulation generator 44 delivered electrical stimulation therapy to patient 12, thereby indicating that processor 40, while implementing the current seizure detection algorithm, detected a target seizure based on a sensed bioelectrical brain signal. The date and time of each target seizure detection based on the bioelectrical brain signal may be stored in memory 42.

Processor 40 also identifies the occurrence of actual target seizures based on the patient activity information (78), as described with respect to FIG. 5. Processor may also confirm that each target seizure detected based on the patient activity information was associated with an abnormal bioelectrical brain signal in order to confirm that the target seizure detected based on the patient activity information was a true seizure. Processor 40 determines whether therapy was delivered to patient 12 for each target seizure identified based on the patient activity information (88). For example, processor 40 may determine whether processor 40, while implementing the current seizure detection algorithm, detected the same target seizures based on the bioelectrical brain signals as those identified based on the patient activity information. As another example, processor 40 may determine whether processor 40, while implementing the current seizure detection algorithm, controlled stimulation generator 44 to deliver therapy to patient 12 around the same time (e.g., within a few seconds or less) as the target seizures indicated by the patient activity information.

If therapy was not delivered for each target seizure identified based on the patient activity information (88), processor 40 may determine that the seizure detection algorithm needs to be adjusted. Accordingly, processor 40 may identify the target seizures identified based on the patient activity information that were not detected based on the bioelectrical brain signal, determine the one or more brain signal characteristics indicative of those missed target seizures (80), and adjust the seizure detection algorithm based on the determined brain signal characteristics (82).

If therapy was delivered for each target seizure identified based on the patient activity information (88), processor 40 may determine that the seizure detection algorithm does not need to be adjusted, and may continue to monitor patient activity information (70) and bioelectrical brain signal information (72) to determine whether therapy is being delivered for each target seizure that is determined based on patient activity information, as described with respect to FIG. 6.

Figure 7:
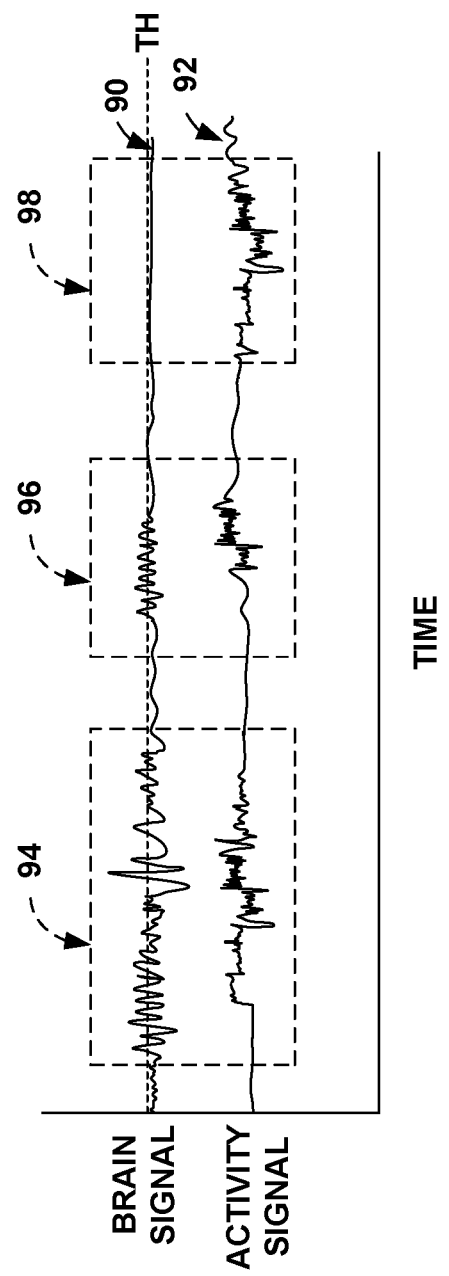
FIG. 7 is a schematic illustration of a bioelectrical brain signal and a patient activity signal, which that indicates the occurrence of a target seizure.

FIG. 7 schematically illustrates bioelectrical brain signal 90 generated by sensing module 46 (FIG. 2) of IMD 16 and patient activity signal 92 generated by activity sensor 36 (FIG. 2) of IMD 16. FIG. 7 illustrates patient activity signal 92 that indicates the occurrence of a target seizure that was not detected by processor 40 based on bioelectrical brain signal 90. In the example shown in FIG. 7, bioelectrical brain signal 90 is an EEG and patient activity signal 92 is generated by a three-axis accelerometer. A three-axis accelerometer generates three signals, i.e., signals indicative of x-axis movement, y-axis movement, and z-axis movement. In FIG. 7, however, only one axis of the activity sensor signal is shown.

Signals 90, 92 are temporally correlated in the example shown in FIG. 7. As previously indicated, processor 40 of IMD 16, while implementing a seizure detection algorithm, detects seizures based on bioelectrical brain signal 90, and controls therapy delivery to patient 12 upon detection of the seizure based on bioelectrical brain signal 90. In the example shown in FIG. 7, processor 40 of IMD 16 detects a seizure based on bioelectrical brain signal 90 at times 94 and 96, and, therefore, IMD 16 delivers stimulation therapy to patient at times 94 and 96.

Processor 40 may implement the technique shown in FIG. 6 to determine whether the seizure detection algorithm implemented by processor 40 to detect a seizure based on bioelectrical brain signal 90 should be adjusted. As shown in FIG. 7, temporally correlating bioelectrical brain signal 90 and patient activity signal 92 helps processor 40 identify whether the seizure detection algorithm implemented by processor 40 is resulting in false negative seizure detections. For example, processor 40 may determine when processor 40, while implementing the current seizure detection algorithm, detected a seizure based on bioelectrical brain signal 90.

In addition, processor 40 may determine when the patient activity signal 92 indicates the occurrence of target seizures, e.g., using the techniques described above with respect to FIGS. 5 and 6. In the example shown in FIG. 7, processor 40 determines that patient activity signal 92 indicates the occurrence of a target seizures at times 94, 96, and 98, but processor 40 only detected the seizure at time 94. Thus, processor 40 failed to detect the target seizure that occurred at times 96 and 98 based on the bioelectrical brain signal. In other examples, activity signal 92 may not indicate the occurrence of target seizures at time 94 because therapy delivery by IMD 16 may be effective in mitigating any involuntary movement resulting from the seizure.

In some examples, prior to adjusting the seizure detection algorithm, processor 40 may determine whether the target seizures at times 96 and 98 that were detected based on patient activity signal 92 were actual seizures. For example, processor 40 may review the temporally correlated brain signal 90 to determine whether brain signal 90 exhibited abnormal activity at the times that patient activity signal 92 indicates an occurrence of a target seizure. In the example shown in FIG. 7, processor 40 determines whether brain signal 90 exhibits abnormal behavior by comparing an amplitude (e.g., an instantaneous, peak, average or median amplitude) of brain signal 90 over a sample period of time to an amplitude threshold. The amplitude threshold is indicated by line TH in FIG. 7. Threshold TH may be determined by a clinician for a particular patient 12 or based on a plurality of patients when the patient(s) are known to be in a non-seizure state when no electrographic seizure is occurring. The amplitude threshold TH is different than any amplitude threshold that may be used to detect a target seizure. In general, amplitude threshold TH merely indicates the amplitude threshold at which brain signal 90 begins to exhibits abnormal activity, although such abnormal activity may not necessarily be an electrographic seizure.

Processor 40 determines that for time period 96, brain signal 90 exhibited an average amplitude that is greater than threshold TH. Accordingly, processor 40 determines that during time period 96, the target seizure detected based on patient activity signal 92 is a true seizure. On the other hand, processor 40 determines that for time period 98, brain signal 90 exhibited normal behavior because an average amplitude of brain signal 90 during time period 98 was less than threshold TH. Based on this determination that brain signal 90 did not exhibit abnormal behavior during time period 98, processor 40 determines that the target seizure detected based on patient activity signal 92 during time period 98 was a false positive detection. For at these reasons, processor 40 adjusts the seizure detection algorithm based on the true target seizure detected during time period 96, but not the false positive target seizure detection associated with during time period 98.

In order to adjust the seizure detection algorithm, processor 40 may determine one or more signal characteristics of bioelectrical brain signal 90 during time period 96 or prior to time period 96. For example, processor 40 may determine a mean, median, highest or lowest amplitude of a period of time immediately preceding time period 96, one or more frequency band characteristics of bioelectrical brain signal 90 preceding or during time period 96, or a signal template generated based on the pattern of bioelectrical brain signal 90 during a predetermined period of time preceding or overlapping with time 96. Processor 40 may then store the determined bioelectrical brain signal characteristics as part of seizure detection algorithm information 56 (FIG. 2), such that processor 40 detects the target seizure associated with the determined bioelectrical brain signal characteristics when implementing the adjusted seizure detection algorithm.

Figure 8:
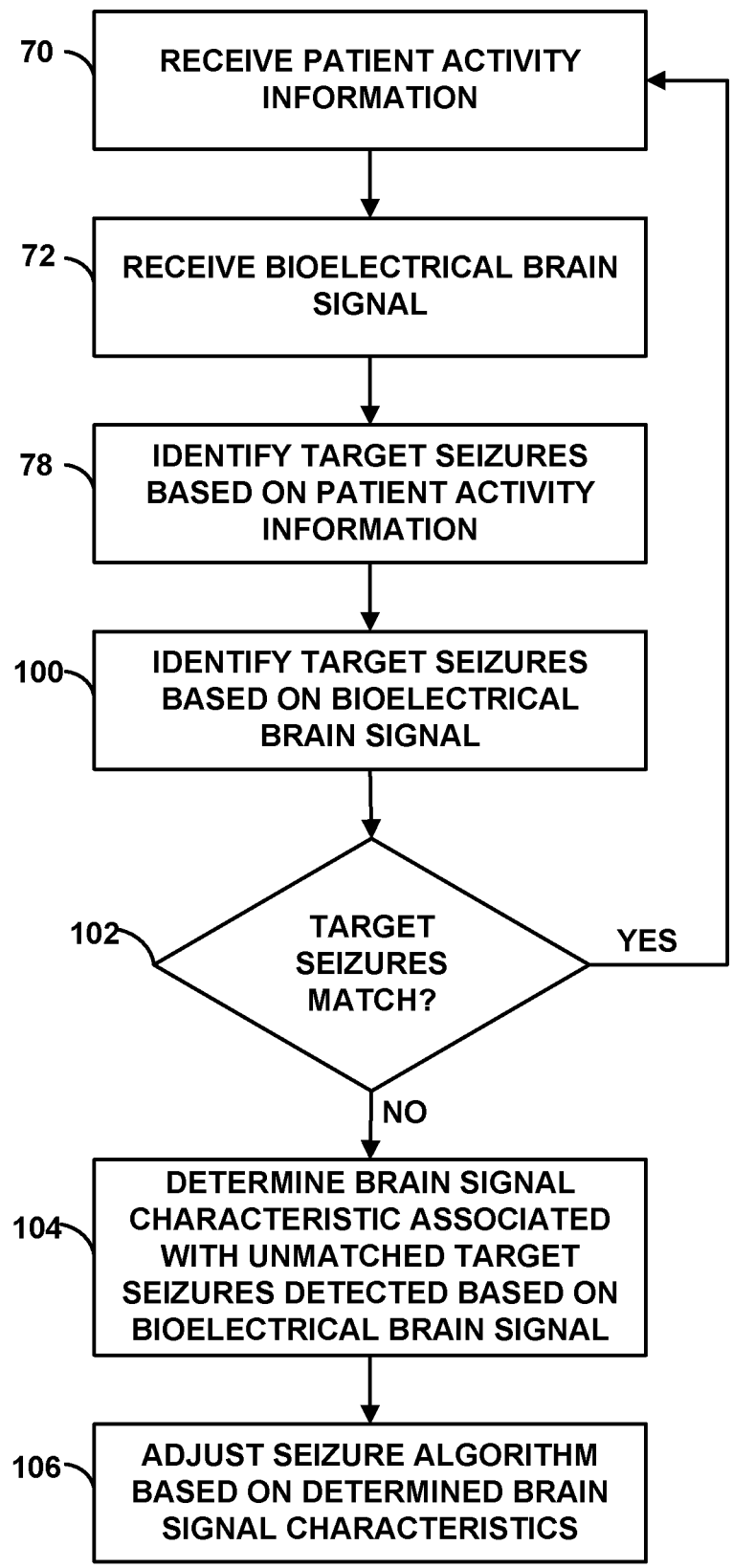
FIG. 8 is a flow diagram of an example technique for adjusting a seizure detection algorithm to minimize the number of false positive target seizure detections.

In some examples, processor 40 may also adjust a seizure detection algorithm to reduce the number of false positive seizure detections. FIG. 8 is a flow diagram illustrating an example technique with which processor 40 may adjust a seizure detection algorithm upon determining that the seizure detection algorithm is mischaracterizing some electrographic seizures as target seizures. As with the technique shown in FIG. 5, processor 40 receives patient activity information, e.g., by receiving a signal from activity sensor 36 (70) and receives a bioelectrical brain signal from sensing module 46 (FIG. 2) (72). Processor 40 identifies target seizures based on patient activity information (78).

In addition, processor identifies target seizures based on a sensed bioelectrical brain signal (100). For example, processor 40 may determine whether processor 40, while implementing the current seizure detection algorithm, detected a seizure that resulted in therapy delivery to patient 12. The seizure detection algorithm indicates the electrographic seizures for which processor 40 controls stimulation generator 44 to generate and deliver therapy to patient 12. As another example, processor 40 may determine when processor 40 controlled stimulation generator 44 to deliver therapy to patient 12, thereby indicating processor 40 detected a target seizure based on a bioelectrical brain signal.

Processor 40 may determine whether the target seizures detected based on the bioelectrical brain signal and patient activity signal match in time (102). That is, processor 40 may determine whether, for each target seizure detected based on the patient activity signal, processor 40 also detected a target seizure based on the bioelectrical brain signal at substantially the same time. Alternatively, processor 40 may determine whether, for each target seizure detected based on the bioelectrical brain signal, processor 40 also detected a target seizure based on the patient activity signal. Processor 40 may determine whether the target seizure detections within a particular period of time (e.g., the preceding hour, selected number of hours, day or more) substantially match.

If the target seizures detected based on the bioelectrical brain signal and patient activity signal substantially match (e.g., about 85% to about 100% match), processor 40 may determine that the seizure detection algorithm does not need to be adjusted because processor 40 is not mischaracterizing an undesirable number of electrographic seizures as target seizures.

On the other hand, if the target seizures detected based on the bioelectrical brain signal and patient activity signal do not substantially match, processor 40 may determine that processor 40 is mischaracterizing an undesirable number of electrographic seizures as target seizures, resulting in false positive target seizure detections. Accordingly, processor 40 may update the stored seizure detection algorithm to minimize the number of false positive detections. In the example shown in FIG. 8, processor 40 determines the bioelectrical brain signal characteristics associated with the target seizures that were detected based on the bioelectrical brain signal, but not detected based on the patient activity signal (104), i.e., the unmatched target seizures. Processor 40 may adjust the seizure detection algorithm to remove the determined bioelectrical brain signal characteristics (106), e.g., to prevent future detection of target seizures based on the determined bioelectrical brain signal characteristics.

In some cases, the technique shown in FIG. 8 may not be useful for adjusting the seizure detection algorithm implemented by IMD 16. For example, in some cases, IMD 16 may detect a target seizure based on a bioelectrical brain signal, the patient activity signal may not reflect the target seizure because therapy delivery by IMD 16 was effective in mitigating involuntary movement resulting from the seizure or preventing the seizure. As a result, the seizure detections based on the bioelectrical brain signal may not match up with a seizure detection based on a patient activity signal. However, in cases in which therapy delivery to patient 12 mitigates a seizure, but does not prevent the seizure or prevent a motor seizure, activity signal 92 may indicate the occurrence of target seizures despite the delivery of therapy to patient 12.

In some cases, the technique shown in FIG. 8 may not only be useful for adjusting the seizure detection algorithm implemented by IMD 16, but also evaluating effectiveness of open-loop or closed-loop therapies. The open-loop or closed-loop therapies may be evaluated using the technique shown in FIG. 8, for example, after a seizure detection algorithm has been implemented. However, the open-loop or closed-loop therapies may be evaluated by determining how many physical manifestations of an actual seizure occurrence are detected at any time throughout the course of therapy delivery by IMD 16.

In some cases, IMD 16 may detect a target seizure based on a bioelectrical brain signal, and the patient activity signal may not reflect the actual occurrence of the target seizure because therapy delivery by IMD 16 was effective in mitigating involuntary movement resulting from the seizure or other physical manifestations of the seizure, or in preventing the seizure. As a result, the seizure detections based on the bioelectrical brain signal may not match up with a seizure detection based on a patient activity signal. The decrease in match rates and/or corresponding reduction in target seizure detections based on the patient activity (relative to a baseline monitoring period) may indicate that the therapy was effective. However, in cases in which therapy delivery to patient 12 mitigates a seizure detected in the bioelectric brain signal, but does not prevent the seizure or prevent a motor seizure, activity signal 92 may indicate the occurrence of target seizures despite the delivery of therapy to patient 12. Failure to observe a decrease in the match rate or reduction in target seizure frequency may indicate changes to therapy parameters are warranted.

Figure 9:
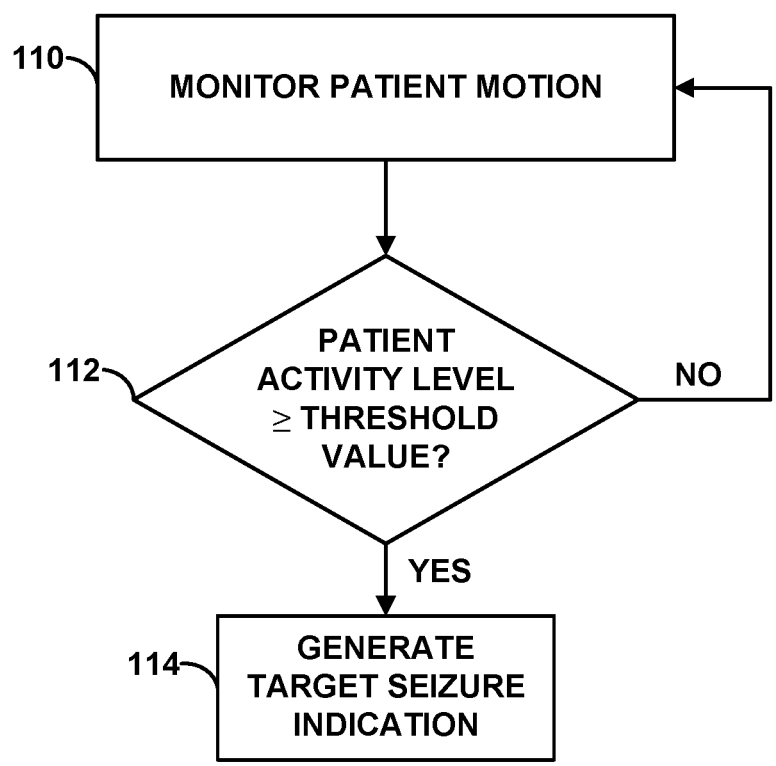
FIG. 9 is a flow diagram of an example technique for identifying a target seizure based on patient activity information.

FIG. 9 is a flow diagram illustrating a technique processor 40 of IMD 16, processor 60 of programmer 14 or a processor of another device may implement in order to determine whether an activity signal characteristic is indicative of a target seizure. Processor 40 of programmer 14 or another device may implement the technique shown in FIG. 9 with the techniques shown in FIGS. 6 and 8 to identify the occurrence of target seizures based on patient activity information. The identification of the occurrence of target seizures based on patient activity information may then be used to adjust a seizure detection algorithm for detecting target seizures based on a bioelectrical brain signal.

Processor 40 of IMD 16 monitors the patient activity (110), e.g., by receiving an electrical signal generated by activity sensor 36 (FIG. 2). Processor 40 may determine whether the amplitude, frequency, or an energy level in a frequency band of the electrical signal generated by activity sensor 36 (i.e., the patient activity signal) over a period of time is greater than or equal to a threshold value (112). The period of time may be selected to be an average duration of a seizure for patient 12 or for a class of patients with similar seizure disorders. The amplitude may be, for example, an instantaneous, mean, median, lowest or highest relative amplitude of the patient activity signal. The threshold value may be stored in IMD 16 or programmer 14.

Characteristics (e.g., amplitude or frequency) of the electrical signal output by activity sensor 36 may vary based on patient activity. Thus, in the example shown in FIG. 9, an amplitude, frequency, energy level in a frequency band or another characteristic of the patient activity signal that is greater than or equal to the threshold value may indicate that the patient activity level exceeded a normal level, thereby indicating an occurrence of a target seizure. Certain types of target seizures, such as tonic-clonic seizures, are characterized by a high level of involuntary movement that exceeds a normal level. Thus, the magnitude of patient activity may be a useful parameter for detecting the occurrence of the target seizure.

In other examples, some target seizures may be characterized by repetitive motion or another pattern of movement, which may be detected by comparing the patient activity signal to a stored template signal. In another example, processor 40 may determine whether the patient activity signal indicates convulsive motion or another pattern of movement by correlating an amplitude waveform of the signal in the time domain or frequency domain to a template signal, determining a change in the amplitude or frequency of the electrical signal over time, comparing a ratio of power in different frequency bands to a stored value, combinations thereof, and the like. For example, a slope of the amplitude of the patient activity signal over time or timing between inflection points or other critical points in the pattern of the amplitude of the electrical signal over time may be compared to trend information indicative of the seizure state movement. Processor 40 may implement an algorithm that recognizes a trend of the patient activity signal that is indicative of a seizure state movement. If the trend of the patient activity signal matches or substantially matches the trend template indicative of convulsive motion, processor 40 may determine a target seizure occurred because of the detection of the seizure state movement.

In some examples, template correlation described herein may include correlating a signal from activity sensor 36 to a template or correlating a mathematically transformed signal from activity sensor 36 to a signal template. Processor 40 may compare the activity sensor signal or a transformed signal to a template or a transformed template. The transform may include, for example, various mathematical transforms.

The template signal or the stored values may be specific to patient 12. For example, patient 12 may undergo motion having a particular pattern during a tonic-clonic seizure, and the pattern may be captured by the template signal or stored values. A clinician may determine the template signal or stored values that indicate a particular motion associated with a seizure or a particular type of seizure during a programming session in which the signal from activity sensor 36 is monitored during one or more seizures and stored as the template. Alternatively, one or more values (e.g., amplitude values) may be extracted from the activity signal monitored during the one or more target seizures of patient 12. In other examples, the template signal or the stored values may be general to more than one patient 12, such as a class of patients having similar seizure disorders.

In another example, processor 40 may perform temporal correlation with one or more templates by sampling the waveform generated by the electrical signal from the activity sensor with a sliding window and comparing the waveform with stored template waveforms that are indicative of the convulsive motion or nonconvulsive motion. In one example, processor 40 may perform a correlation analysis by moving a window along a digitized plot of the amplitude waveform of the electrical signal from activity sensor 36 at regular intervals, such as between about one millisecond to about ten millisecond intervals, to define a sample of the electrical signal. The sample window may be slid along the plot until a correlation is detected between a waveform of a template stored within memory 42 (FIG. 2) of IMD 16 or memory 62 (FIG. 3) of programmer 14 and the waveform of the sample of the electrical signal from activity sensor 36 defined by the window.

In other examples, some target seizures may be detected by processor 40 (or processor 60 of programmer 14) by determining whether patient 12 exhibited a sudden change in patient posture that indicates that patient 12 fell. The techniques for detecting a sudden change in patient posture may be determined using similar techniques for detecting seizure state motion (e.g., involuntary motion occurring during a target seizure). For example, processor 40 may correlate an amplitude waveform of the signal output by activity sensor 36 in the time domain or frequency domain to a template signal that is associated with a sudden change in patient posture or a sudden movement. A correlation between the signal from activity sensor 36 and the template signal may indicate a patient fall. As another example, processor 40 may determine a change in the amplitude or frequency of the electrical signal over time and compare the change over time to a threshold value. A relatively large change in the amplitude of the electrical signal from activity sensor 36 over time may indicate a relatively sudden change in patient posture or a sudden movement, which may indicate the detected seizure is related to a fall by patient 12. Memory 42 of IMD 16 or memory 62 of programmer 14 may store the threshold value that indicates a minimum change in amplitude of electrical signal from activity sensor 36 that is associated with a relatively sudden change in patient posture or a sudden movement.

As previously described, patient posture may also be determined based on intracranial pressure of patient 12. A sudden change in posture (determined based on intracranial pressure) correlated with a detected seizure may indicate a patient fall.

Upon determining the patient activity signal is indicative of a target seizure, processor 40 may generate a target seizure indication (114), which may be a value, flag or other generated marker stored in memory 42 of IMD 16. The date and time of the target seizure indication may also be stored in memory 42. The target seizure indication may later be associated with a bioelectrical brain signal to determine whether the seizure detection algorithm should be adjusted. For example, processor 40 may temporally correlate stored target seizure indications with a bioelectrical brain signal and determine whether processor 40 is mischaracterizing some seizures detected based on the bioelectrical brain signal as target seizures or missing the detection of some seizures based on the bioelectrical brain signal, as described with reference to FIGS. 6 and 8.

Examples of therapy systems that deliver therapy to patient 12 in response to detection of a seizure are described herein. These types of systems may be referred to as closed loop therapy systems. In some examples, therapy delivery to patient 12 may be open loop, such that IMD 16 delivers electrical stimulation to patient 12 without any feedback from a sensor that controls the timing of the stimulation. In an open loop therapy system, IMD 16 may deliver stimulation to patient 12 according to a schedule determined by a clinician or programmed into IMD 16 by the manufacturer. The schedule may set forth regular times for stimulation delivery (e.g., delivery of therapy for five minutes at ten minute intervals), or irregular times for stimulation delivery (e.g., less frequent stimulation at night when patient 12 is sleeping).

In some cases, determination of whether target seizures are occurring based on a signal from one or both activity sensors 25, 36 may be useful for determining whether the open loop stimulation is effective. As previously indicated, delivering stimulation to brain 28 may help "exercise" the neural networks and provide long term seizure disorder therapy to patient 12 by minimizing the number of seizures that occur. An indication from one or both sensors 25, 36 that target seizures (e.g., motor seizures) are still occurring may indicate that more frequent stimulation is desirable, e.g., to increase the "exercising" of the neural networks of brain 28.

In some examples in which IMD 16 delivers therapy in an open loop, IMD 16 may monitor patient activity from one or both sensors 25, 36 or another type of sensor that is indicative of patient activity associated with a seizure, and store the activity information for later analysis by a clinician. A clinician may later retrieve the information and determine that a modification to the frequency with which the stimulation is delivered to patient 12 is desirable.

Figure 10:
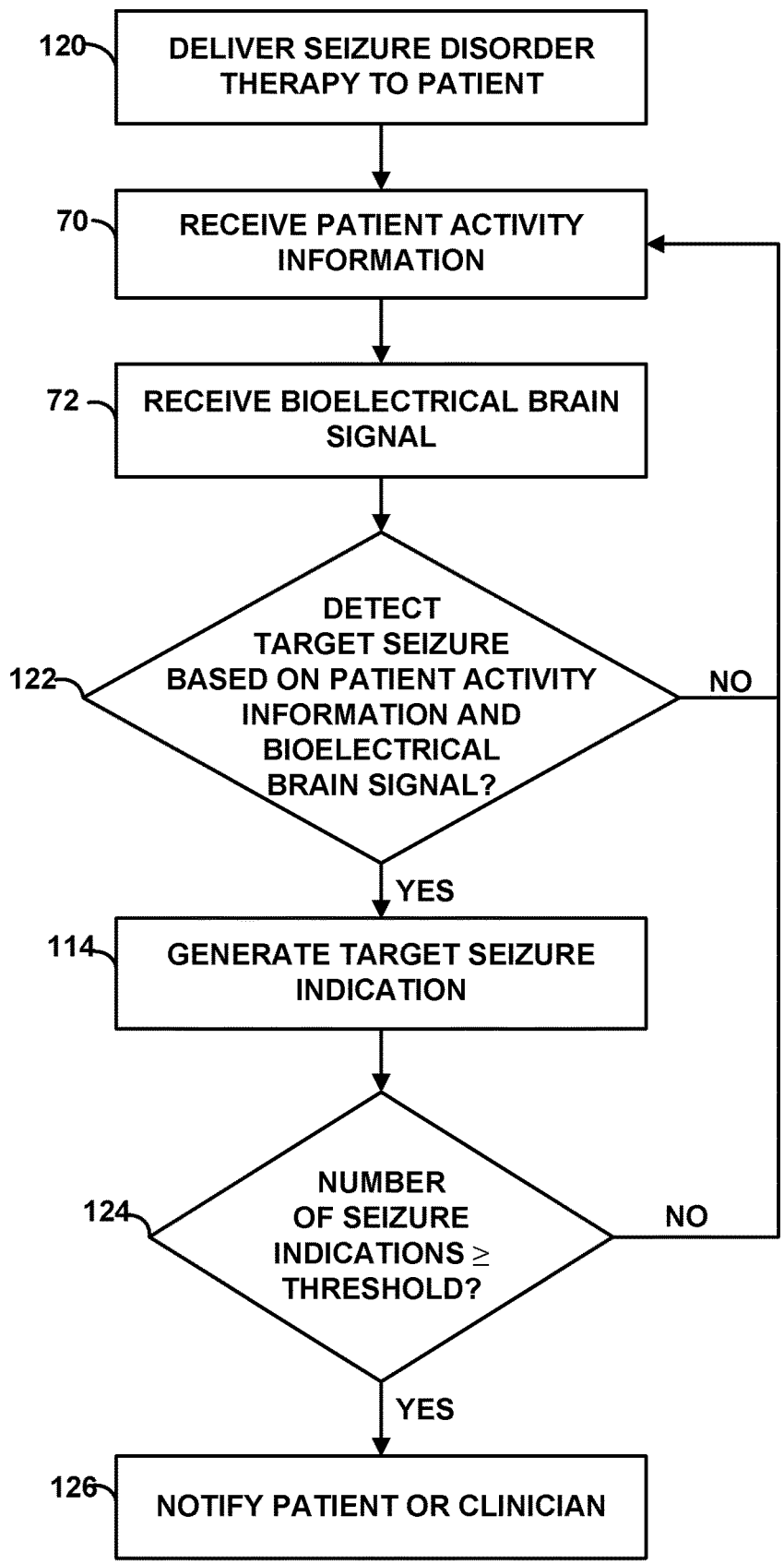
FIG. 10 is a flow diagram of an example technique for monitoring an efficacy of seizure disorder therapy.

FIG. 10 is a flow diagram of an example technique for monitoring an efficacy of seizure disorder therapy. IMD 16 delivers seizure disorder therapy to patient 12 (120) in an open loop manner (e.g., on a substantially regular basis) or in a closed loop manner (e.g., based on detection of a prospective seizure). Processor 40 receives patient activity information from one or both activity sensors 25, 36 (70) and a bioelectrical brain signal sensed by sensing module 46 (72). Based on the patient activity information and the bioelectrical brain signal, processor 40 determines whether a target seizure has occurred (122). In some examples, processor 40 compares an amplitude (e.g., a peak, mean, median or instantaneous) of the bioelectrical brain signal to a threshold amplitude, comparing a trend in a waveform of the bioelectrical signal over time to a template, or compares a frequency domain characteristic (e.g., a power level within one or more frequency bands) of the bioelectrical brain signal to a threshold power level to detect a seizure based on the bioelectrical brain signal. Upon detection of the seizure based on the bioelectrical brain signal, processor 40 determines whether the seizure is a target seizure based on the patient activity signal. For example, processor 40 may determine whether the patient activity signal is indicative of a motor component of a target seizure, e.g., using the technique shown in FIG. 9.

In other examples, processor 40 first determines whether the patient activity signal is indicative of a motor component of a target seizure and subsequently determines whether the correlated bioelectrical brain signal is also indicative of a target seizure. If a target seizure is detected using either technique, processor 40 generates a target seizure indication (114), which, as discussed above, may be a value, flag or other generated marker stored in memory 42 of IMD 16. Processor 40 determines whether a number of target seizure indications that have been generated for patient 12 is greater than or equal to a threshold value (124). In some examples, processor 40 determines whether a number of target seizure indications generated within a predetermined range of time (e.g., a certain number of days, weeks or even months) is greater than or equal to a threshold value (124).

The threshold value may be stored in memory 42 of IMD 16 or a memory of another device. In some examples, the clinician selects the threshold value as well as the time range for counting the number of target seizure indications for comparing to the threshold value. If the number of seizure indications is not greater than or equal to the threshold value, processor 40 may continue monitoring the patient activity information (70) and bioelectrical brain signal information (72) until another target seizure is detected (122).

If the number of seizure indications is greater than or equal to the threshold value, processor 40 generates a notification to notify patient 12, a patient caretaker, or a clinician (126). The notification may indicate that an undesirable number of target seizures have been detected despite the delivery of seizure disorder therapy. Upon receipt of the notification, patient 12 may seek medical attention, at which time the clinician may adjust the intensity of therapy delivery, or, in examples in which IMD 16 delivers closed loop therapy to patient 12, the clinician may adjust the seizure detection algorithm with which IMD 16 detects seizures. In other examples, patient 12 may initiate the adjustment to therapy delivery or the adjustment to a seizure detection algorithm with the aid of programmer 14. Other courses of action are also contemplated.

The techniques described in this disclosure, including those attributed to programmer 14, IMD 16, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 40 of IMD 16 and/or processor 60 of programmer 14, any one or more parts of the techniques described herein may be implemented by a processor of one of IMD 16, programmer 14, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples of the disclosure have been described. These and other examples are within the scope of the following example statements.

The invention claimed is:

1. A method comprising:
receiving, by processing circuitry, a first signal indicative of a physiological parameter of a patient, wherein the physiological parameter comprises a bioelectrical brain signal;
receiving, by the processing circuitry, a second signal indicative of a patient parameter of the patient, wherein the patient parameter comprises at least one of patient motion, patient posture, intracranial pressure, respiration rate, heart rate, or muscle activity;
identifying, by the processing circuitry and using a seizure detection algorithm, a target seizure based on at least one characteristic of the first signal;
determining, by the processing circuitry, that the second signal did not indicate the target seizure;
determining, by the processing circuitry, that stimulation therapy was not delivered to the patient in association with the target seizure;
in response to determining that the second signal did not indicate the target seizure and that the stimulation therapy was not delivered, adjusting, by the processing circuitry, the seizure detection algorithm to not identify the target seizure based on the at least one characteristic of the first signal; and
controlling, according to the adjusted seizure detection algorithm, delivery of subsequent stimulation therapy to the patient.

2. The method of claim 1, wherein adjusting the seizure detection algorithm comprises removing the at least one characteristic from the seizure detection algorithm.

3. The method of claim 1, wherein the at least one characteristic comprises an amplitude of the first signal.

4. The method of claim 1, wherein the at least one characteristic comprises a frequency of the first signal.

5. The method of claim 1, wherein the at least one characteristic comprises an energy level in a frequency band of the first signal.

6. The method of claim 1, wherein the at least one characteristic comprises at least one of an amplitude, a frequency, or an energy level in a frequency band of the first signal greater than or equal to a threshold value.

7. The method of claim 1, wherein the target seizure is a first target seizure, and wherein the method further comprises:
identifying, using the adjusted seizure detection algorithm, a second target seizure of the patient; and
responsive to identifying the second target seizure using the adjusted seizure detection algorithm, controlling a stimulation generator to deliver the subsequent stimulation therapy to a brain of the patient.

8. The method of claim 1, wherein the target seizure is a first target seizure, and wherein the method further comprises:
identifying, using the adjusted seizure detection algorithm, a second target seizure of the patient; and
responsive to identifying the second target seizure using the adjusted seizure detection algorithm, controlling an external programmer to present an alert indicating that the target seizure was identified.

9. The method of claim 1, wherein an implantable medical device comprises the processing circuitry and is configured to deliver the subsequent stimulation therapy.

10. A system comprising:
a first sensor configured to generate a first signal indicative of a physiological parameter of a patient, wherein the physiological parameter comprises a bioelectrical brain signal;
a second sensor configured to generate a second signal indicative of a patient parameter of the patient, wherein the patient parameter comprises at least one of patient motion, patient posture, intracranial pressure, respiration rate, heart rate, or muscle activity; and processing circuitry configured to:
identify, using a seizure detection algorithm, a target seizure based on at least one characteristic of the first signal;
determine that the second signal did not indicate the target seizure;
determine that stimulation therapy was not delivered to the patient in association with the target seizure;
in response to determining that the second signal did not indicate the target seizure and that the stimulation therapy was not delivered, adjust the seizure detection algorithm to not identify the target seizure based on the at least one characteristic of the first signal; and
control, based on the adjusted seizure detection algorithm and subsequent first, delivery of stimulation therapy to the patient.

11. The system of claim 10, wherein the processing circuitry is configured to adjust the seizure detection algorithm by at least removing the at least one characteristic from the seizure detection algorithm.

12. The system of claim 10, wherein the at least one characteristic comprises an amplitude of the first signal.

13. The system of claim 10, wherein the at least one characteristic comprises a frequency of the first signal.

14. The system of claim 10, wherein the at least one characteristic comprises an energy level in a frequency band of the first signal.

15. The system of claim 10, wherein the at least one characteristic comprises at least one of an amplitude, a frequency, or an energy level in a frequency band of the first signal greater than or equal to a threshold value.

16. The system of claim 10, wherein the stimulation therapy comprises electrical stimulation therapy, and wherein the system further comprises a stimulation generator configured to deliver the electrical stimulation therapy, wherein the target seizure is a first target seizure, and wherein the processing circuitry is further configured to:
identify, using the adjusted seizure detection algorithm, a second target seizure of the patient; and
responsive to identifying the second target seizure using the adjusted seizure detection algorithm, control the stimulation generator to deliver the subsequent electrical stimulation therapy to a brain of the patient.

17. The system of claim 10, further comprising an external programmer, wherein the target seizure is a first target seizure, and wherein the processing circuitry is further configured to:
identify, using the adjusted seizure detection algorithm, a second target seizure of the patient; and
responsive to identifying the second target seizure using the adjusted seizure detection algorithm, control the external programmer to present an alert indicating that the second target seizure was identified.

18. The system of claim 10, further comprising an implantable medical device comprising the processing circuitry and a stimulation generator configured to generate the subsequent stimulation therapy.

19. The system of claim 10, further comprising an external programmer comprising the processing circuitry.

20. A system comprising:
a first sensor configured to generate a first signal indicative of a physiological parameter of a patient, wherein the physiological parameter comprises a bioelectrical brain signal;
a second sensor configured to generate a second signal indicative of a patient parameter of the patient, wherein the patient parameter comprises at least one of patient motion, patient posture, intracranial pressure, respiration rate, heart rate, or muscle activity; and
processing circuitry configured to:
determine that a target seizure is not detected based on both the first signal and the second signal;
determine that stimulation therapy was not delivered to the patient in association with the target seizure; and
in response to determining that the target seizure is not detected based on both the first signal and the second signal and that the stimulation therapy was not delivered, adjust the seizure detection algorithm; and
control, based on the adjusted seizure detection algorithm and subsequent delivery of stimulation therapy to the patient.

21. The system of claim 20, wherein the processing circuitry is configured to determine that the target seizure is not detected based on both the first signal and the second signal by at least:
identifying the target seizure using the seizure detection algorithm based on the first signal; and
determining that the target seizure is not identified by the second signal.

22. The system of claim 21, wherein the processing circuitry is configured to adjust the seizure detection algorithm by at least removing at least one characteristic of the first signal from the seizure detection algorithm.

23. The system of claim 20, wherein the processing circuitry is configured to determine that the target seizure is not detected based on both the first signal and the second signal by at least:
identifying the target seizure based on the second signal; and
determining that the target seizure is not identified by the seizure detection algorithm based on the first signal.

* * * * *